United States Patent [19]
O'Neill et al.

[11] Patent Number: 5,755,686
[45] Date of Patent: May 26, 1998

[54] ANTEGRADE/RETROGRADE SWITCH FOR CARDIOPLEGIA CANNULAE

[75] Inventors: William G. O'Neill, Ann Arbor; Nelson L. Huldin, Pittsfield Township, Washtenaw County; Lawrence R. Jones, Manchester, all of Mich.

[73] Assignee: Minnesota Mining and Manufacturing Company, St. Paul, Minn.

[21] Appl. No.: 790,410

[22] Filed: Jan. 29, 1997

Related U.S. Application Data

[63] Continuation of Ser. No. 380,072, Jan. 30, 1995, abandoned.

[51] Int. Cl.⁶ .................................................. A61M 31/00
[52] U.S. Cl. ......................... 604/53; 604/97; 604/99; 604/249; 251/324
[58] Field of Search .......................... 604/30, 33, 49, 604/52, 53, 96–99, 246, 249, 264, 280, 283; 251/318, 324, 325

[56] References Cited

U.S. PATENT DOCUMENTS

| | | | |
|---|---|---|---|
| D. 359,801 | 6/1995 | Boykin et al. | D24/112 |
| 3,678,959 | 7/1972 | Liposky | 137/625.11 |
| 3,833,013 | 9/1974 | Leonard | 137/171 |
| 3,859,985 | 1/1975 | Eckhart | 128/2.05 |
| 4,397,335 | 8/1983 | Doblar et al. | 137/625.19 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |
| 4,512,163 | 4/1985 | Wells et al. | 62/394 |
| 4,566,480 | 1/1986 | Parham | 137/271 |
| 4,668,215 | 5/1987 | Allgood | 604/30 |
| 4,846,177 | 7/1989 | Leonard | 128/400 |
| 4,883,455 | 11/1989 | Leonard | 604/4 |
| 4,927,412 | 5/1990 | Menasche | 604/96 |
| 4,979,942 | 12/1990 | Wolf et al. | 604/83 |
| 5,047,015 | 9/1991 | Foote et al. | 604/99 |
| 5,057,078 | 10/1991 | Foote et al. | 604/99 |
| 5,082,025 | 1/1992 | DeVries et al. | 137/863 |
| 5,084,031 | 1/1992 | Todd et al. | 604/248 |
| 5,247,966 | 9/1993 | Stevens et al. | 137/625 |
| 5,318,534 | 6/1994 | Williams et al. | 604/97 |
| 5,324,260 | 6/1994 | O'Neill et al. | 604/96 |
| 5,360,406 | 11/1994 | Boykin et al. | 604/170 |
| 5,395,331 | 3/1995 | O'Neill et al. | 604/96 |
| 5,401,244 | 3/1995 | Boykin et al. | 604/53 |
| 5,403,281 | 4/1995 | O'Neill et al. | 604/113 |
| 5,423,749 | 6/1995 | Merte et al. | 604/67 |
| 5,423,769 | 6/1995 | Jonkman et al. | 604/250 |
| 5,443,453 | 8/1995 | Walker et al. | 604/248 |
| 5,464,388 | 11/1995 | Merte et al. | 604/153 |
| 5,466,216 | 11/1995 | Brown et al. | 604/33 |

FOREIGN PATENT DOCUMENTS

WO 91/18632  12/1991  WIPO ........................ A61M 5/00

OTHER PUBLICATIONS

Partington, article covering the background for the use of antegrade/retrograde cardioplegic in combination submitted to the journal of Thoracic and Cardiovascular Surgery, date unknown.

GISH Biomedical, Inc.—Directions for Use—Cardioplegia Systems (Jan. 1991).

Research Medical, Inc.—RMI–006 Retrograde–Antegrade Cardioplegia Kit (Apr. 1991).

DLP, Inc.—Label for "Ariss—Antegrade/Retrograde Y".

*Primary Examiner*—Corrine M. McDermott
*Attorney, Agent, or Firm*—Gary L. Griswold; Robert W. Sprague; Stephen W. Bauer

[57] ABSTRACT

A switch for selectively directing fluid to either one of two catheters and for inflating a "manually" inflatable balloon of one of the catheters when fluid is directed to that catheter. The switch includes a valve mechanism that is operatively linked with a balloon inflation mechanism such that the balloon is inflated when fluid is directed to that catheter, and the balloon is deflated when fluid is directed to the other catheter. The switch is particularly adapted for use in administering cardioplegia solution to a patient's heart alternatively via an antegrade cardioplegia catheter and a retrograde cardioplegia catheter. A method of use of the switch is also disclosed.

62 Claims, 11 Drawing Sheets

ANTEGRADE/RETROGRADE SWITCH FOR CARDIOPLEGIA CANNULAE

This application is a continuation of application Ser. No. 08/380,072 filed Jan. 30, 1995, now abandoned.

This invention relates to a switch for directing fluid to either one of two catheters, and more particularly to an antegrade/retrograde switch for directing fluid to either an antegrade or retrograde cardioplegia catheter.

BACKGROUND OF THE INVENTION

Cardioplegia solution is used during heart surgery to stop the beating of the heart and reduce its temperature, to thereby preserve the heart during surgery. Cardioplegia solution is typically administered to the patient's heart either via a coronary artery with an antegrade cardioplegia catheter, or via a coronary vein, e.g., the coronary sinus, with a retrograde cardioplegia catheter. As used herein, "antegrade" means in the direction of normal blood flow, for example, in a coronary artery in the direction toward capillaries, and "retrograde" means in the direction opposite to normal blood flow, for example, in a coronary vein in the direction toward capillaries. The term "cardioplegia solution" includes conventional potassium solutions, blood and mixed blood/potassium solutions, as well as any other cardioplegia solution.

Antegrade cardioplegia catheters have been sold under the trade designation "SARNS™ antegrade/vent cardioplegia catheter" (Catalog Nos. 164660 (12 gauge) 164665 (14 gauge)), and "SARNS™ antegrade cardioplegia catheter" (Catalog Nos. 164650 (12 gauge) and 15465 (14 gauge)) by Minnesota Mining and Manufacturing Company, St. Paul, Minn. Antegrade cardioplegia catheters typically do not have inflatable retention balloons but may have pressure sensing lumens for sensing pressure within the aortic root. Antegrade cardioplegia catheters are inserted into the aortic root, which feeds the coronary arteries.

Retrograde cardioplegia catheters typically have an inflatable retention balloon that secures the distal end of the retrograde catheter in the coronary sinus. Such retention balloons may be inflated in one of two ways: (1) "manually" via a balloon inflation lumen that is separate from the infusion lumen of the catheter, or (2) "automatically" via an aperture between the interior of the balloon and the infusion lumen of the catheter such that cardioplegia solution being infused by the catheter inflates the balloon.

As used here, the term "separate" means the balloon inflation lumen is not in fluid communication with the infusion lumen of the catheter, although the balloon inflation lumen and infusion lumen may only be separated by a thin wall. The term "inflatable balloon" includes balloons that are pressurized and depressurized, and which may have a generally pear-shaped or other bulbous configuration even when not inflated, or which are adapted to lay flat against the body of the catheter when not inflated.

Manually inflatable retention balloons allow much greater control of the inflation of the balloon than do auto-inflatable balloons, and this control may be exercised independently of the flow of cardioplegia solution through the catheter. Inflation of auto-inflatable retention balloons can only be controlled by varying the amount of cardioplegia solution being infused through the catheter.

Retrograde cardioplegia catheters also typically include pressure monitoring lumens and outlets for monitoring pressure within the coronary sinus. Retrograde catheters are inserted via the right atrium into the coronary sinus via either a "blind" or "open atrium" technique as discussed in U.S. Pat. No. 5,324,260.

Retrograde cardioplegia catheters are disclosed in U.S. Pat. No. 5,395,331, which are hereby incorporated herein by reference.

During surgery, it may be desirable to switch between administering cardioplegia in the antegrade and retrograde directions in order to improve perfusion of the heart with cardioplegia solution. An ability to switch between antegrade and retrograde administration is believed to be particularly desirable where coronary artery blockage is severe, or when "warm" cardioplegia is administered.

Switches have been available that switch cardioplegia solution between an antegrade cardioplegia catheter and a retrograde cardioplegia catheter having an auto-inflatable balloon. See, for example, U.S. Pat. Nos. 5,082,025 and 5,084,031.

U.S. Pat. No. 5,082,025 (DeVries et al.) discloses an antegrade-retrograde switch and occluder and system for using the same. That switch is used with a tubing set including a Y-connector, with the switch directing fluid from a source of cardioplegia solution to either one of the legs of the "Y".

U.S. Pat. No. 5,084,031 (Todd et al.) discloses a cardioplegia three-way double stopcock. That stopcock directs cardioplegia solution to either an antegrade or retrograde catheter and also switches between pressure monitoring ports in fluid communication with the pressure monitoring lumens of the antegrade and retrograde catheters.

In the switches disclosed in U.S. Pat. Nos. 5,082,025 and 5,084,031, an auto-inflatable balloon of a retrograde catheter is inflated by the cardioplegia solution directed through the infusion lumen of the retrograde catheter. Neither of those patents disclose a mechanism for simultaneously and automatically inflating a balloon of a manually-inflatable type retrograde catheter when cardioplegia solution is directed to the retrograde catheter.

Various cardioplegia administration systems and components are disclosed in U.S. Pat. Nos. 4,416,280; 4,427,009; 4,433,971; 4,512,163; 4,846,177 and 4,883,455, 5,403,281 and 5,423,749.

SUMMARY OF THE INVENTION

This invention provides a switch that is adapted to direct fluid to either one of two catheters, including a catheter that includes a retention balloon that is inflated via an inflation lumen separate from its infusion lumen, and inflating the retention balloon of one of those catheters at the same time that fluid is directed through the infusion lumen of that catheter. This invention provides such a switch that is particularly useful in switching the flow of cardioplegia solution between an antegrade cardioplegia catheter and a retrograde cardioplegia catheter having a "manually-inflatable" retention balloon, and thereby selectively administer cardioplegia solution to a patient's heart in antegrade or retrograde directions. This invention further provides such a switch that is reliable and easy to use.

This invention provides such a switch that allows manually-controllable inflation of the retention balloon of the retrograde cardioplegia catheter while providing an automatic link between act of switching the flow of cardioplegia solution between the antegrade and retrograde catheters and inflation of the retention balloon of the retrograde catheter. The surgeon retains the ability to determine the amount of inflation of the retention balloon within a relevant range of pressures.

Generally, an antegrade/retrograde switch of the invention comprises balloon inflation means for inflating the balloon of the retrograde coronary sinus catheter. The balloon inflation means comprises an inflation chamber for fluid, a port into the chamber for bringing the inflation chamber into fluid communication with the manually inflatable balloon of the retrograde coronary sinus catheter, and actuating means. The actuating means is selectively operable for driving fluid out of the inflation chamber through the port, whereby fluid is driven into the balloon of the retrograde coronary sinus catheter to inflate the balloon, and for drawing fluid through the port into the inflation chamber, whereby fluid is drawn out of the balloon of the retrograde coronary sinus catheter into the inflation chamber to deflate the balloon. Valve means is provided for selectively directing cardioplegia solution from a source of cardioplegia solution to either one of the antegrade catheter and the retrograde catheter. The actuating means and the valve means are operatively connected such that, when the actuating means inflates the balloon of the retrograde catheter, the valve means directs cardioplegia solution to the retrograde catheter, and, when the actuating means deflates the balloon of the retrograde catheter, the valve means directs cardioplegia solution to the antegrade catheter.

Preferably, the actuating means is movable within the inflation chamber between a first position, wherein the fluid is within the inflation chamber and the balloon is deflated, and a second position, wherein fluid has been driven out of the inflation chamber by the actuating means to inflate the balloon.

Also, preferably, the actuating means comprises a piston slidingly received in the inflation chamber in sealing engagement with walls defining the inflation chamber, with the valve means being provided in the piston and the walls defining the inflation chamber.

Most preferably, a switch housing has the walls defining the inflation chamber, with the piston having side walls generally adjacent the walls defining the inflation chamber and movable therealong. The valve means comprises a retrograde passageway through the wall defining the inflation chamber, an antegrade passageway through the wall defining the inflation chamber, a cardioplegia supply passageway through the wall defining the inflation chamber, and a valve passageway defined by the piston. The retrograde passageway includes a first connector for connecting tubing in fluid communication with the retrograde passageway to provide cardioplegia solution to the retrograde catheter. The antegrade passageway includes a second connector for connecting tubing in fluid communication with the antegrade passageway to provide cardioplegia solution to the antegrade catheter. The cardioplegia supply passageway including a third connector for connecting tubing in fluid communication with the cardioplegia supply passageway to provide cardioplegia solution to the cardioplegia supply passageway. The valve passageway brings the cardioplegia supply passageway and antegrade passageway into fluid communication when the piston is in its first position, and the valve passageway brings the cardioplegia supply passageway and retrograde passageway into fluid communication when the piston is in its second position. The piston prevents fluid communication between the retrograde passageway and cardioplegia supply passageway when the piston is in its first position, and the piston prevents fluid communication between the antegrade passageway and the cardioplegia supply passageway when the piston is in its second position.

Also, preferably, a lever is pivotable mounted on the switch housing and operatively connected to the piston to move the piston between its first and second positions. A rod extends from the piston and has a rack portion with teeth. A pinion is provided on the lever, and the pinion has teeth in intermeshing engagement with the teeth of the rack portion of the rod to move the piston as the lever is pivoted.

Most preferably, the piston includes has at least two annular sealing rings extending along the circumference of the piston and defining the valve passageway along the circumference of the piston between the two annular sealing rings.

In a second aspect of the invention, the antegrade/retrograde switch generally comprises a housing having internal walls defining an inflation chamber and a valve chamber. The housing has:

A. A port into the inflation chamber and a first connector on the port for connecting tubing in fluid communication with a balloon of a retrograde catheter.

B. An inlet into the valve chamber and a second connector on the inlet for connecting tubing in fluid communication with a source of cardioplegia solution.

C. A retrograde outlet from the valve chamber and a third connector on the retrograde outlet for connecting tubing in fluid communication with an infusion lumen of a retrograde catheter.

D. An antegrade outlet from the valve chamber and a fourth connector on the antegrade outlet for connecting tubing in fluid communication with an infusion lumen of an antegrade catheter.

An actuator member is provided in the inflation chamber in sealing engagement with the walls of the housing defining the inflation chamber, and a valve member is provided in the valve chamber in sealing engagement with the walls of the housing defining the valve chamber. The actuator member and valve member are operatively linked for movement between:

1. A first position, wherein the actuator member is spaced from the port of the inflation chamber whereby the balloon of the retrograde catheter is deflated, and the valve member is positioned between the inlet and the retrograde outlet to direct cardioplegia solution from the inlet through the antegrade outlet; and 2. A second position, wherein the actuating member is closer to the port of the inflation chamber than in the first position whereby the balloon of the retrograde catheter is inflated, and the valve member is positioned between the inlet and the antegrade outlet to direct cardioplegia solution from the inlet through the retrograde outlet.

Preferably, a single handle is provided, which is operatively linked with the actuating member and valve member. The handle is adapted for manually moving the actuating member and valve member between their first and second positions.

In a third aspect of the invention, a cardioplegia administration system is provided for selectively administering cardioplegia solution to a patient's heart in the antegrade direction via the arterial system of the heart or in the retrograde direction via the venous system of the heart. The system generally comprises an antegrade catheter having an infusion lumen for administering cardioplegia solution to a patient's heart via the arterial system of the heart in the antegrade direction, a retrograde catheter having an infusion lumen for administering cardioplegia solution to a patient's heart via the venous system of the heart in the retrograde direction, and an antegrade/retrograde switch as described as either the first and second aspects of the invention above.

The retrograde catheter includes an inflatable retention balloon for retaining the retrograde catheter in position in the patient's heart, and an inflation lumen, separate from the infusion lumen, in fluid communication with the balloon for providing fluid to the balloon to inflate the balloon and for draining fluid from the balloon to deflate the balloon. Antegrade tubing is provided in fluid communication with the infusion lumen of the antegrade catheter for providing cardioplegia solution to the infusion lumen of the antegrade catheter, and retrograde tubing is provided in fluid communication with the infusion lumen of the retrograde catheter for providing cardioplegia solution to the infusion lumen of the retrograde catheter. Balloon-inflation tubing is provided in fluid communication with the inflation lumen of the retrograde catheter for supplying and draining fluid to and from the retention balloon to inflate and deflate the retention balloon. A source of cardioplegia solution is also provided, as is cardioplegia supply tubing in fluid communication with the source of cardioplegia solution.

In a fourth aspect of the invention, an antegrade/retrograde switch generally comprises a switch housing having internal walls defining an inflation chamber for fluid, a port into the inflation chamber for bringing the inflation chamber into fluid communication with the manually inflatable balloon of the retrograde coronary sinus catheter; and piston in sealing engagement with the internal walls defining the inflation chamber. The piston is selectively movable within the inflation chamber from a first position to a second position for driving fluid out of the inflation chamber through the port, whereby fluid is driven into the balloon of the retrograde coronary sinus catheter to inflate the balloon. The piston is also selectively movable from the second position to the first position for drawing fluid through the port into the inflation chamber, whereby fluid is drawn out of the balloon of the retrograde coronary sinus catheter into the inflation chamber to deflate the balloon. Retrograde, antegrade and cardioplegia supply passageways are provided through the internal wall defining the inflation chamber. The retrograde passageway includes a first connector for connecting tubing in fluid communication with the retrograde passageway to provide cardioplegia solution to the retrograde catheter, and the antegrade passageway includes a second connector for connecting tubing in fluid communication with the antegrade passageway to provide cardioplegia solution to the antegrade catheter. The cardioplegia supply passageway includes a third connector for connecting tubing in fluid communication with the cardioplegia supply passageway to provide cardioplegia solution to the cardioplegia supply passageway. A valve passageway is defined by the piston. The valve passageway brings (a) the cardioplegia supply passageway and antegrade passageway into fluid communication when the piston is in its first position, and (b) the cardioplegia supply passageway and retrograde passageway into fluid communication when the piston is in its second position. As a result, when the piston inflates the balloon of the retrograde catheter, the valve passageway directs cardioplegia solution to the retrograde catheter, and when the piston deflates the balloon of the retrograde catheter, the valve passageway directs cardioplegia solution to the antegrade catheter.

In a fifth aspect of the invention, a switch is provided for selectively directing a first fluid to either one of a first catheter and a second catheter, the second catheter being of the type including an infusion lumen, an inflatable balloon and a balloon inflation lumen, separate from the infusion lumen, for inflating and deflating the balloon. The switch generally comprises a housing, valve means and balloon inflation means. The housing has first, second, third and fourth ports. The first port is adapted to be connected in fluid communication with the first catheter; the second port is adapted to be connected in fluid communication with the infusion lumen of the second catheter; the third port is adapted to be connected in fluid communication with a source of the first fluid; and the fourth port is adapted to be connected in fluid communication with the balloon inflation lumen of the second catheter. The valve means is adapted for selectively directing fluid from the source of the first fluid to the first and second catheters. The valve means includes a valve member movable between (1) a first position, in which the valve means brings the first and third ports but not the second port into fluid communication with each other, whereby first fluid is directed from the source of the first fluid to the first catheter, and (2) a second position, in which the valve means brings the second and third ports but not the first port into fluid communication with each other, whereby the first fluid is directed from the source of the first fluid to the second catheter. The balloon inflation means is operatively linked with the valve means and is adapted for expelling a second fluid out through the fourth port when the valve member of the valve means is moved to its second position and for drawing the second fluid in through the fourth port when the valve member of the valve means is moved to its first position. As a result, the balloon of the second catheter is deflated when the first fluid is directed to the first catheter, and the balloon of the second catheter is inflated with the second fluid when the first fluid is directed to the second catheter.

In a sixth aspect of the invention, a method is provided for administering cardioplegia solution selectively in the antegrade direction via the arterial system of a patient's heart and in the retrograde direction via the venous system of the patient's heart. The method generally comprises the following steps:

A. Inserting a retrograde coronary sinus catheter into a patient's coronary sinus. The coronary sinus catheter includes an infusion lumen for supplying cardioplegia solution to a patient's heart, an inflatable retention balloon for engaging the walls of the coronary sinus to retain the catheter in position, and a balloon inflation lumen, separate from the infusion lumen, for inflating the inflatable retention balloon.

B. Inserting an antegrade catheter into a coronary artery. The antegrade catheter includes an infusion lumen for supplying cardioplegia solution to a patient's heart.

C. Providing a source of cardioplegia solution.

D. Connecting an antegrade/retrograde switch via tubing to the retrograde coronary sinus catheter, the antegrade catheter and a source of cardioplegia solution. The antegrade/retrograde switch includes (1) valve means for selectively directing cardioplegia solution supplied to switch from the source of cardioplegia solution to the infusion lumen of either of the retrograde coronary sinus catheter and the antegrade catheter, and (2) balloon inflation means for inflating the retention balloon of the coronary sinus catheter with fluid via the balloon inflation lumen when the valve means directs cardioplegia solution to the infusion lumen of the retrograde coronary sinus catheter and for deflating the retention balloon via the balloon inflation lumen when the valve means directs cardioplegia solution to the infusion lumen of the antegrade catheter.

D. Actuating the valve means to direct cardioplegia solution to the antegrade catheter with the retention balloon of the retrograde catheter deflated by the balloon inflation means of the switch.

E. Actuating the valve means to direct cardioplegia solution to infusion lumen of the retrograde catheter with the balloon inflation means inflating the retention balloon via the balloon inflation lumen to help retain the retrograde catheter in position in the coronary sinus. Other features will pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
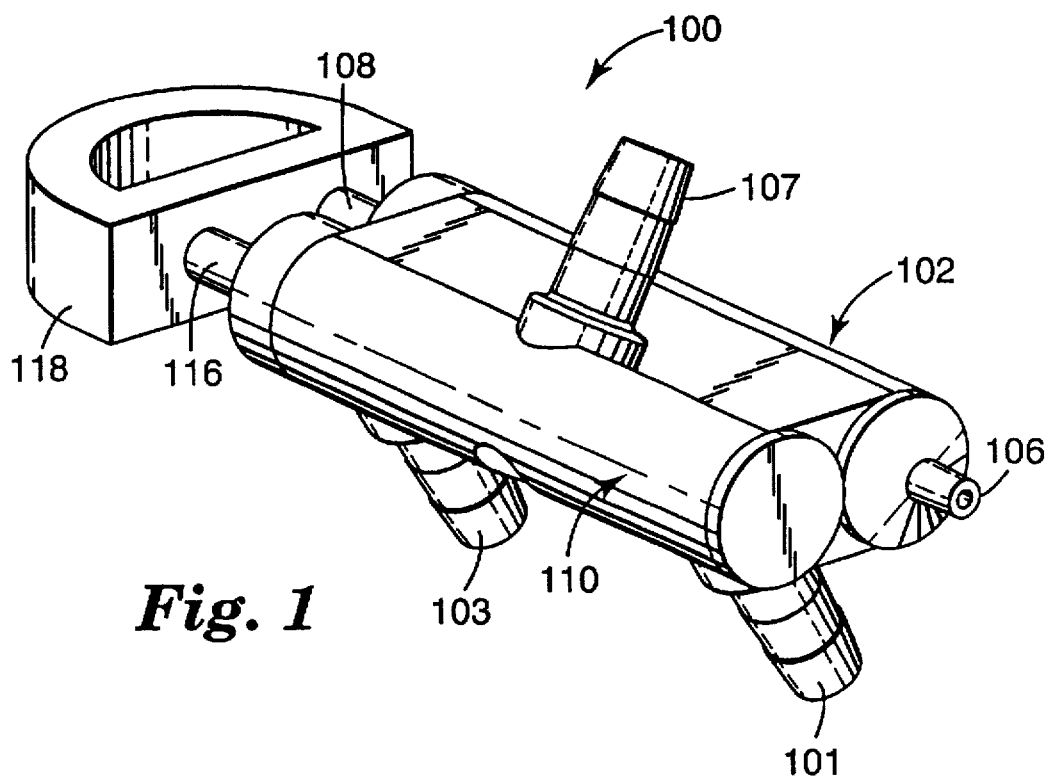
FIG. 1 is perspective view of a first embodiment of an antegrade/retrograde switch of the invention.
Figure 2:
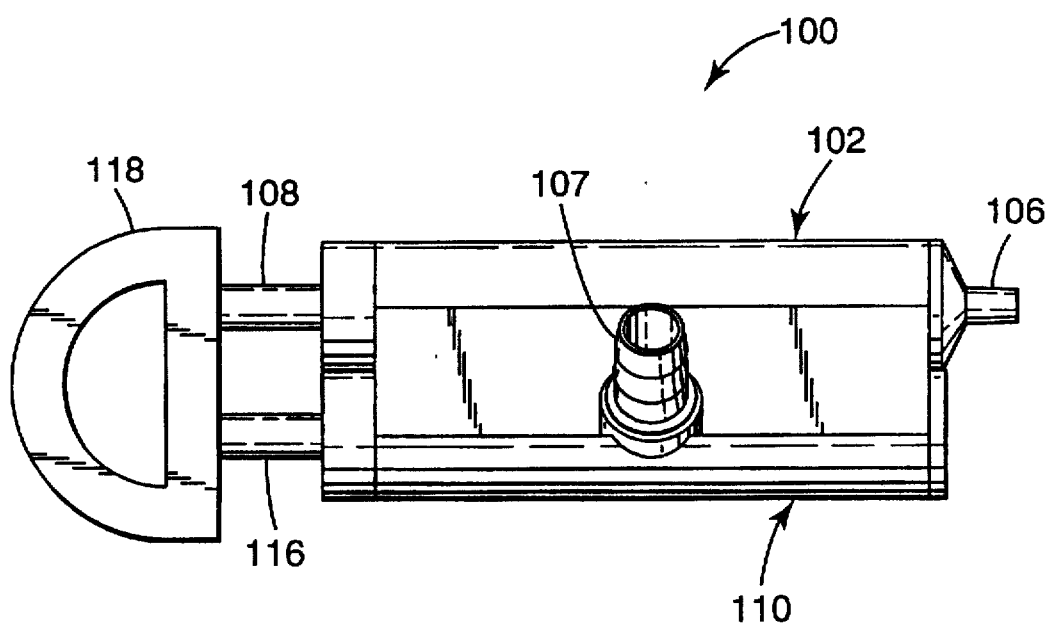
FIG. 2 is a top plan view of the antegrade/retrograde switch of FIG. 1.

Now referring to the drawing, a switch of the first embodiment of the invention is indicated in its entirety by the reference numeral 200 in FIGS. 1-4, and a switch of the second embodiment of the invention is indicated in its entirety by the reference numeral 100 in FIGS. 5-17. The switch 100, 200 is particularly adapted for selectively directing the flow of cardioplegia solution to either one of an antegrade cardioplegia catheter 22 (FIGS. 3 and 4) and a retrograde cardioplegia catheter 24 having a "manually-inflatable" retention balloon 26, although it will be understood that there may be other uses for the switch 100, 200. Retrograde cardioplegia catheter 24 is also known as a coronary sinus catheter 24.

Examples of suitable antegrade cardioplegia catheters 22 are the antegrade catheters sold under the trade designation "SARNS™ antegrade/vent cardioplegia catheter" (Catalog Nos. 164660 (12 gauge) 164665 (14 gauge)), and "SARNS™ antegrade cardioplegia catheter" (Catalog Nos. 164650 (12 gauge) and 15465 (14 gauge)) by Minnesota Mining and Manufacturing Company, St. Paul, Minn. It is also contemplated that the switch 100, 200 of the invention could be used with an antegrade catheter having a pressure sensing lumen for sensing pressure within the aortic root.

Antegrade tubing 23 is provided in fluid communication with the infusion lumen of the antegrade catheter 22 and an antegrade port 101 or 201 of the antegrade/retrograde switch 100 or 200 for providing cardioplegia solution to the infusion lumen of the antegrade catheter 22.

Examples of suitable manually-inflatable and auto-inflatable retrograde cardioplegia catheters are disclosed in U.S. Pat. Nos. 4,927,412 and 5,324,260 and 5,395,331, which are incorporated herein by reference. Examples of suitable stylets for guiding such retrograde cardioplegia catheters into the coronary sinus of a patient's heart are disclosed in U.S. Pat. Nos. 5,360,406 5,401,244 and D-359, 801, which are incorporated herein by reference.

Figure 3:
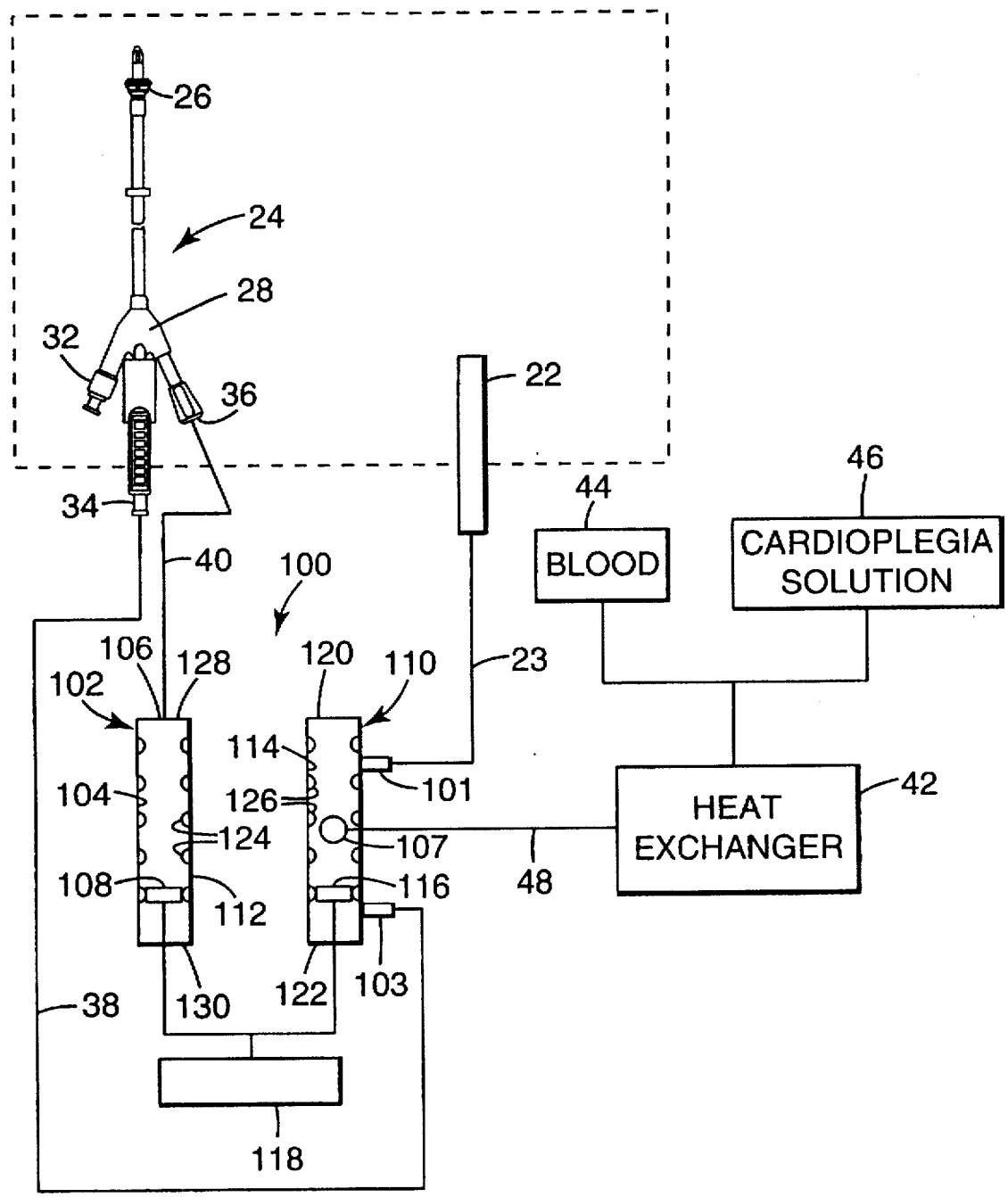
FIG. 3 is a schematic view of a cardioplegia administration system including the antegrade/retrograde switch of FIGS. 1 and 2, illustrating the switch directing cardioplegia solution to the antegrade catheter with the retention balloon of a retrograde catheter deflated.
Figure 4:
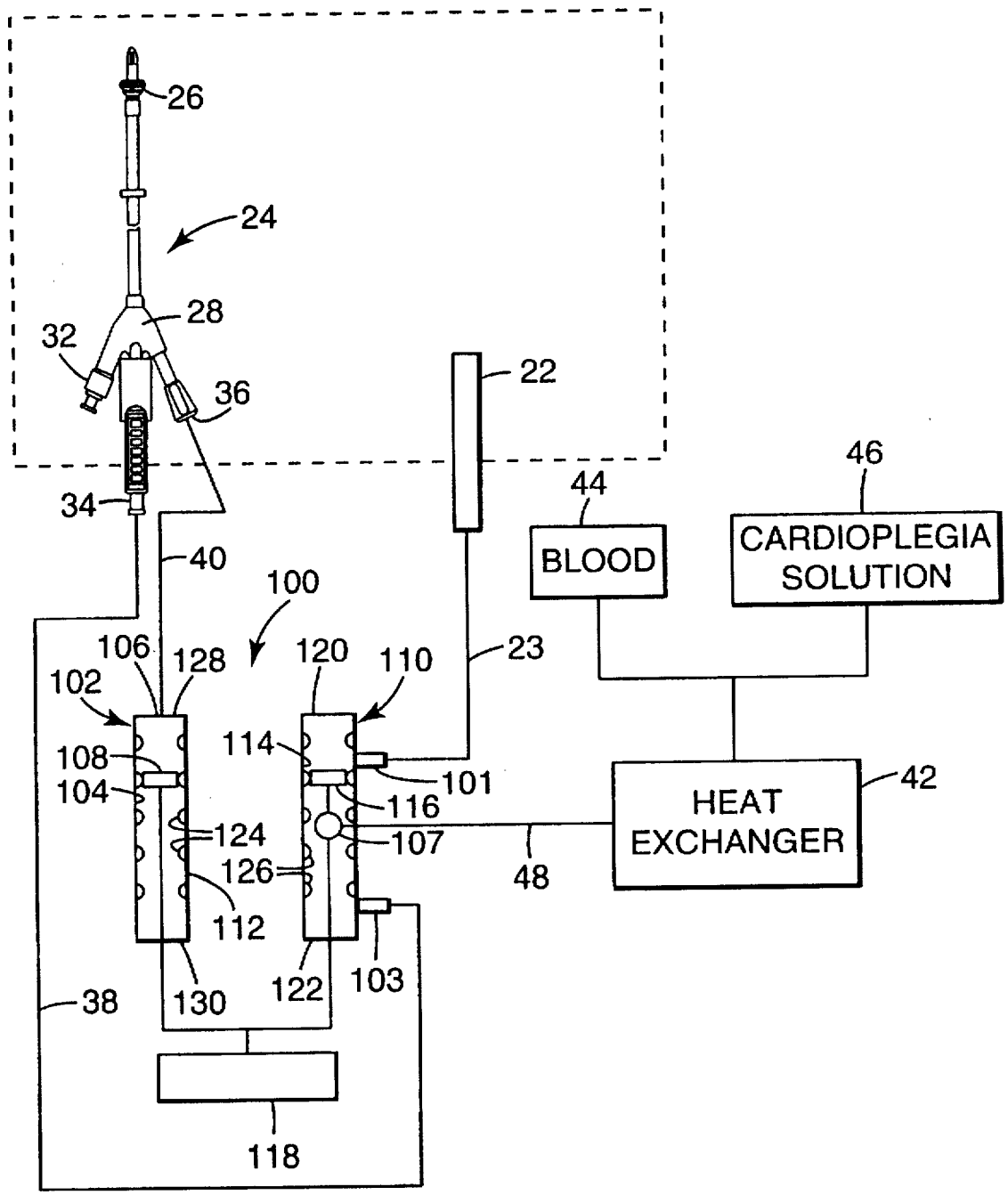
FIG. 4 is a schematic view similar to FIG. 3 illustrating the switch directing cardioplegia solution to the retrograde catheter and inflating the retention balloon of the retrograde catheter.
Figure 5:
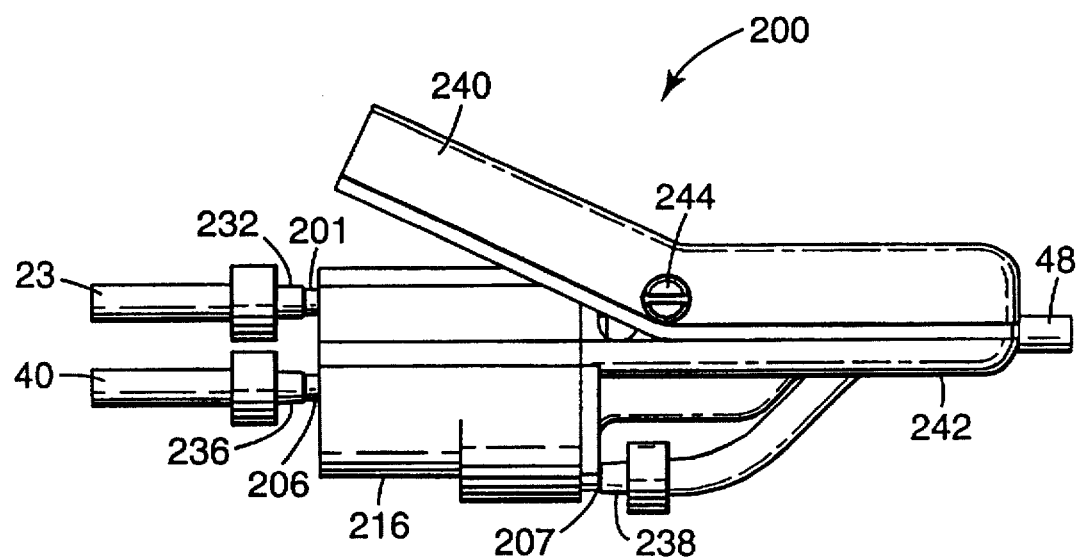
FIG. 5 is a side elevational view of a second embodiment of the antegrade/retrograde switch of the invention.
Figure 6:
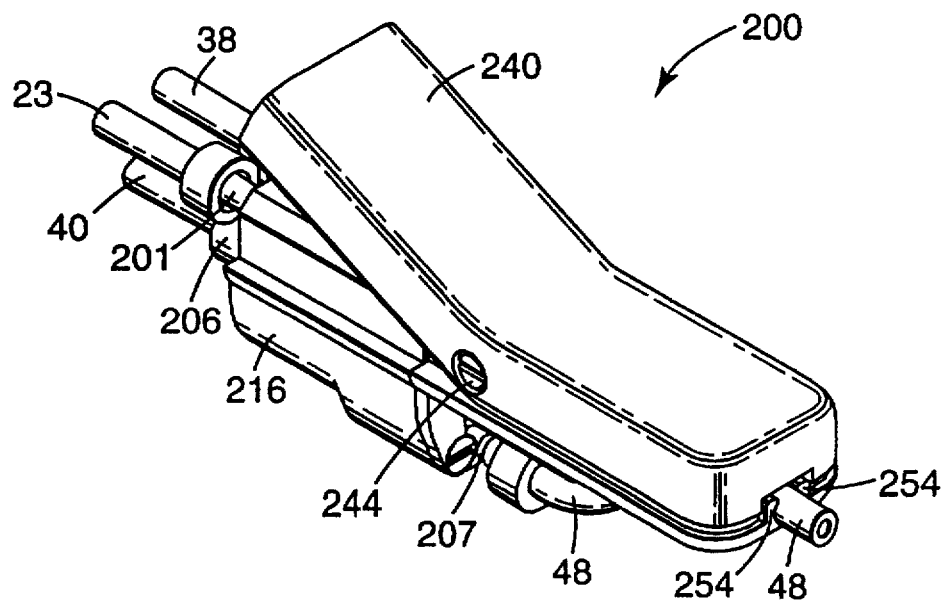
FIG. 6 is a perspective view of the antegrade/retrograde switch of FIG. 5.

Such retrograde catheters 24 also include a pressure sensing lumen for sensing pressure within the coronary sinus. FIGS. 3 and 4 show a retrograde catheter 24 having a three-way, Y-type connection assembly 28, which includes a connector 32 for a pressure sensing line (not shown), as well as connector 34 for the infusion lumen and connector 36 for the balloon inflation lumen.

Retrograde tubing 38 is provided in fluid communication with the infusion lumen of the retrograde catheter 24 and a retrograde port 103 or 203 of the antegrade/retrograde switch 100 or 200 for providing cardioplegia solution to the infusion lumen of the retrograde catheter 24. Balloon-inflation tubing 40 is provided in fluid communication with the inflation lumen of the retrograde catheter 24 and an inflation port 106 or 206 of the antegrade/retrograde switch 100 or 200 for supplying fluid to and draining fluid from the retention balloon 26 to inflate and deflate the retention balloon 26. The retrograde tubing 38 is connected to the connector 34 for the infusion lumen and the balloon-inflation tubing 40 is connected to the connector 36 for the balloon inflation lumen.

A source of cardioplegia solution is also provided. This may conveniently take the form of a heat exchanger 42, a connection to a port of a blood reservoir or blood oxygenating apparatus providing blood 44 and a reservoir 46 of cardioplegia solution, to thereby allow perfusion of "pure" cardioplegia solution, blood and mixed blood/cardioplegia solution. See, for example, allowed U.S. Pat. No. 5,423,749, which is incorporated herein by reference and which discloses a system that is adapted for mixing and administering cardioplegia solution. See, also, U.S. Pat. Nos. 4,846,177, 4,883,455 and 5,403,281, which are also incorporated herein by reference. The source of cardioplegia solution also preferably includes a bubble trap to trap any bubbles in cardioplegia solution, for example, such as disclosed in U.S. Pat. No. 4,883,455.

Cardioplegia supply tubing 48 is provided in fluid communication with the source of cardioplegia solution, e.g., heat exchanger 42 and a cardioplegia supply port 107 or 207 of the antegrade/retrograde switch 100 or 200.

Generally, an antegrade/retrograde switch 100, 200 comprises balloon inflation means 102 or 202 for inflating the retention balloon 26 of the retrograde coronary sinus catheter 24. The balloon inflation means 102 or 202 comprises (a) an inflation chamber 104 or 204 for fluid, (b) a port 106 or 206 into the inflation chamber 104 or 204 for bringing the inflation chamber 104 or 204 into fluid communication with the manually inflatable retention balloon 26 of the retrograde coronary sinus catheter 24, and (c) actuating means 108 or 208. The balloon-inflating fluid may be, for example, air or saline solution.

The actuating means 108 or 208 is selectively operable for driving fluid out of the inflation chamber 104 or 204 through the port 106 or 206, whereby fluid is driven into the retention balloon 26 of the retrograde coronary sinus catheter 24 to inflate the retention balloon 26, and for drawing fluid through the port 106 or 206 into the inflation chamber 104 or 204, whereby fluid is drawn out of the retention balloon 26 of the retrograde coronary sinus catheter 24 into the inflation chamber 104 or 204 to deflate the balloon 26.

Valve means 110 or 210 is provided for selectively directing cardioplegia solution from a source of cardioplegia solution to either one of the antegrade catheter 22 and the retrograde catheter 24. The actuating means 108 or 208 and the valve means 110 or 210 are operatively connected such that, (a) when the actuating means 108 or 208 inflates the retention balloon 26 of the retrograde catheter 24, the valve means 110 or 210 directs cardioplegia solution to the retrograde catheter 24, and, (b) when the actuating means 108 or 208 deflates the retention balloon 26 of the retrograde catheter 24, the valve means 110 or 210 directs cardioplegia solution to the antegrade catheter 22.

Figure 9:
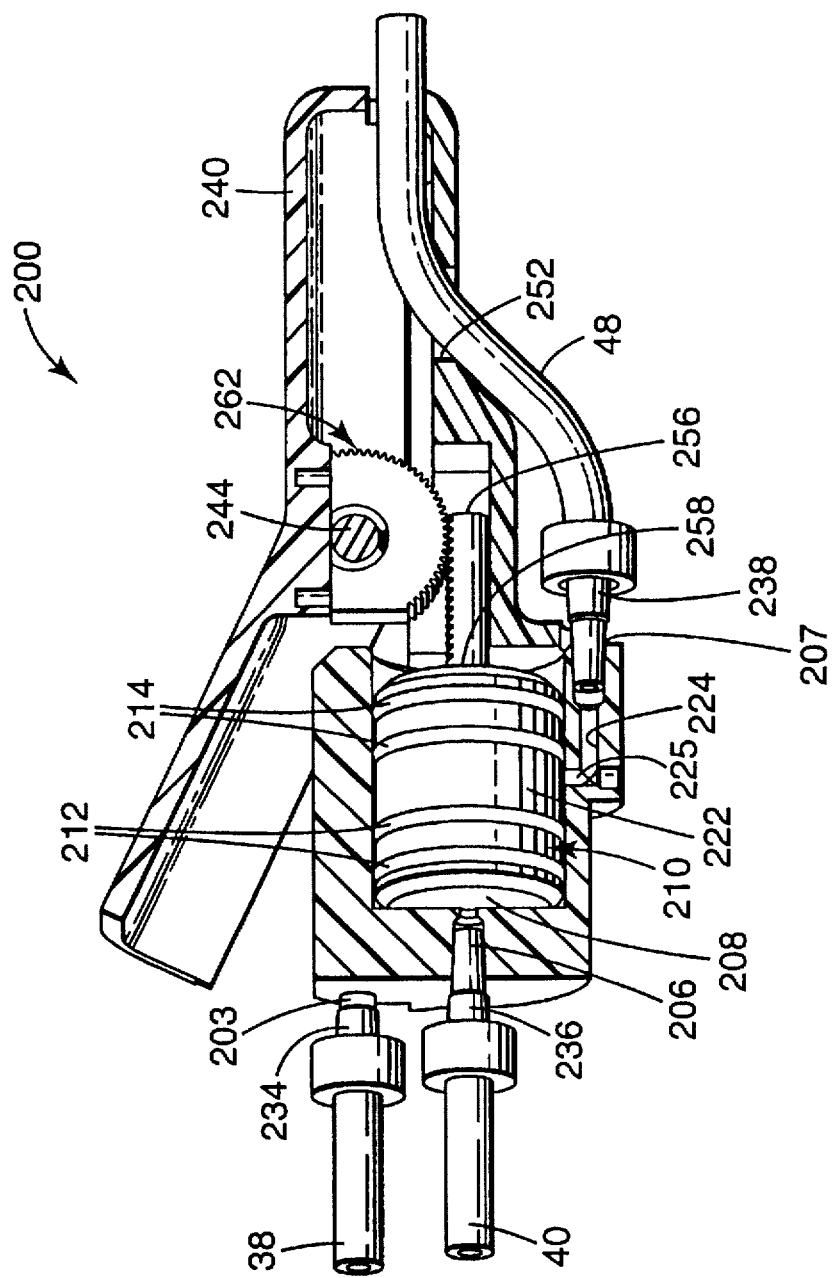
FIG. 9 is a cross-sectional view similar to FIG. 8 illustrating a second position in which cardioplegia solution is directed to the retrograde catheter and the retention balloon of the retrograde catheter is inflated.

As illustrated in FIGS. 3, 4, 8 and 9, the actuating means 108 or 208 is movable within the inflation chamber 104 or 204 between a first position (FIGS. 3 and 8) and a second position (FIGS. 4 and 9). In the first position (FIGS. 3 and 8), the fluid is within the inflation chamber 104 or 204 and the retention balloon 26 of the retrograde catheter 24 is deflated. In the second position (FIGS. 4 and 9), fluid has been driven out of the inflation chamber 104 or 204 by the actuating means 108 or 208 to inflate the retention balloon 26 of the retrograde catheter.

Now referring more particularly to the antegrade/retrograde switch 100 of FIGS. 1–4, the balloon inflation means 102 comprises a syringe or assembly 112 defining the inflation chamber 104 as being generally cylindrical, and a plunger 108, constituting the actuating means 108, movable within the inflation chamber 104 for pressurizing and depressurizing the retention balloon 26 of the retrograde catheter 24.

The valve means 110 comprises a generally cylindrical valve chamber 114 and a valve member 116 movable within the valve chamber 114 between first and second positions (FIGS. 3 and 4, respectively). The valve chamber 114 has an inlet or cardioplegia supply port 107 in fluid communication with the cardioplegia supply tubing 48, a retrograde outlet or port 103 adapted to be in fluid communication with the retrograde catheter 24 via retrograde tubing 38, and an antegrade outlet or port 101 adapted to be in fluid communication with the antegrade catheter 22 via antegrade tubing 23.

The antegrade and retrograde outlets 101 and 103 are located generally adjacent the opposite ends 120 and 122 of the valve chamber 114 relative to one another, and the inlet 107 is located generally between the antegrade and retrograde outlets 101 and 103.

In the valve member's first position (FIG. 3), the antegrade outlet 101 is in fluid communication with the inlet 107 of the valve chamber 114 and the retrograde outlet 103 is blocked. As shown in FIG. 3, the valve member 116 is positioned between the inlet 107 and the retrograde outlet 103, thus blocking fluid communication between the inlet 107 and the retrograde outlet 103 while permitting fluid communication between the inlet 107 and the antegrade outlet 101.

In the valve member's second position (FIG. 4), the retrograde outlet 103 is in fluid communication with the inlet 107 of the valve chamber 114 and the antegrade outlet 101 is blocked. As shown in FIG. 4, the valve member 116 is positioned between the inlet 107 and the antegrade outlet 101, thus blocking fluid communication between the inlet 107 and the antegrade outlet 101 while permitting fluid communication between the inlet 107 and the retrograde outlet 103.

Preferably, the actuating means 108 of the balloon inflation means 102 comprises a first plunger 108 movable within the inflation chamber 104 along a first longitudinal axis of motion between its first and second positions (FIGS. 3 and 4, respectively). The first plunger 108 includes a head in sealing engagement with the walls defining the inflation chamber 104, and a rod extending from the head in the direction away from the balloon inflation port 106.

The valve member 116 comprises a second plunger 116 movable within the valve chamber 114 along a second longitudinal axis of motion generally parallel with the first longitudinal axis of motion between its first and second positions in generally the same direction as the first plunger 108. The second plunger 116 includes a head in sealing engagement with the walls defining the valve chamber 114, and a rod extending from the head.

The heads of each of the first and second plungers 108 and 116 are formed of elastomeric material or include elastomeric sealing members, for example, elastomeric sealing rings, in slidable sealing engagement with the internal walls defining the inflation chamber 104 and valve chamber 114, respectively. Most preferably, the internal walls defining at least one of the inflation chamber 104 and valve chamber 114 include internal annular rings 124 or 126 providing stops 124 or 126 within the chambers 104 and 114. These stops 124 and 126 can be overcome by manually operating the handle 118 but resist movement of the plungers 108 and 116 in response to pressure, for example, pressure within the inflation chamber 104. The internal walls defining the inflation chamber 104 and valve chamber 114 could alternatively be smooth without such annular rings 124 or 126.

The first and second plungers 108 and 116 are connected such that the first and second plungers 108 and 116 are simultaneously moved in generally the same direction between the first and second positions. For example, a handle 118 may be provided, operatively linking the first and second plungers 108 and 116, for manually and simultaneously moving the first and second plungers 108 and 116 between their first and second positions. The handle 118 is most preferably mounted directly to the rods of the first and second plungers 108 and 116.

The balloon inflation means 102 may further comprise an inflation housing (also 102) defining the inflation chamber 104 as being generally elongate having a longitudinal axis coaxial with the first longitudinal axis of motion of the first plunger 108; and the valve means 110 may further comprise a valve housing (also 110) defining the valve chamber 114 as being generally elongate having a longitudinal axis coaxial with the second longitudinal axis of motion of the second plunger 116 and generally parallel with the longitudinal axis of the inflation chamber 104.

The inflation chamber 104 has opposite ends 128 and 130 generally adjacent the opposite ends 120 and 122 of the valve chamber 114. The opposite ends 128, 130, 120 and 122 of each of the inflation and valve chambers 104 and 114 comprise (1) a first end 130 and 122, with the handle 118 extending outwardly from the first ends 130 and 122 of the inflation and valve chambers 104 and 114; and (2) a second end 128 and 120 opposite the first ends 130 and 122. The balloon inflation port 106 of the inflation chamber 104 extends from the second end 128 of the inflation chamber, and the antegrade outlet 101 of the valve chamber 114 is generally adjacent the second end 120 of the valve chamber 114. The retrograde outlet 103 of the valve chamber 114 is generally adjacent the first end 122 of the valve chamber 114. When the plungers 108 and 116 are in their second positions (FIG. 4), this arrangement results in fluid pressure within the valve chamber 114 tending to push the second plunger 116 in the direction toward the second end 120 of the valve chamber 114. At the same time, pressure from the inflated retention balloon 26, which is in fluid communication with the inflation chamber 104, tends to push the first plunger 108 in the direction toward the first end 130 of the inflation chamber 104. The result is that these two forces tend to counteract one another, thereby reducing the net force on the plungers 108 and 116 and making the job of stops 124 and 126 easier.

Most preferably, the inflation housing 102 and valve housing 110 are integrally molded of synthetic resin material. Suitable synthetic resin materials include thermoplastic and thermoset materials, for example, polycarbonate, although other materials may be acceptable.

The switch 100 could alternatively include a second valve chamber (not shown) for switching between pressure sensing lumens in the antegrade and retrograde catheters to bring such sensing lumens into fluid communication with a single pressure sensing line when the respective catheter is infusing cardioplegia solution. It will be appreciated that such a second valve chamber could be similar to valve chamber 114 and would include a valve member or plunger (not shown) operatively linked with first and second plungers similar to plungers 108 and 116.

FIGS. 5–17 illustrate a second preferred embodiment of the invention, in which the antegrade/retrograde switch 200 includes a single actuator or piston 208 which is slidably movable within the balloon inflation chamber 204 to provide both the balloon inflation mechanism and the valve mechanism.

Elastomeric sealing rings 212 and 214 are provided along the circumference of the generally cylindrical piston 208 for slidable-sealing engagement with the internal walls of the switch housing 216 that define the inflation chamber 204. Most preferably, sealing rings 212 and 214 are arranged as two pairs 212 and 214 of sealing rings received in parallel pairs of annular grooves 218 and 220 formed in the circumferential side walls of the piston 208. A valve passageway 222 is defined along the circumference of the piston 208 between pair 212 and pair 214 of the sealing rings. The sealing rings 212 and 214 may be conventional "O-rings" formed of any suitable elastomeric material, for example, silicone. The valve passageway 222 constitutes part of the valve means 210.

Figure 13:
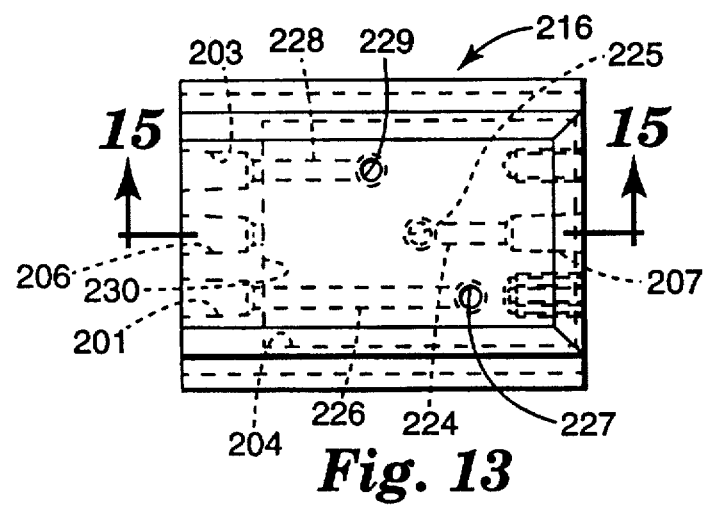
FIG. 13 is a top plan view of a housing of the antegrade/retrograde switch of FIGS. 5-12, illustrating passages for cardioplegia solution and balloon inflation fluid and an inflation chamber in phantom.
Figure 14:
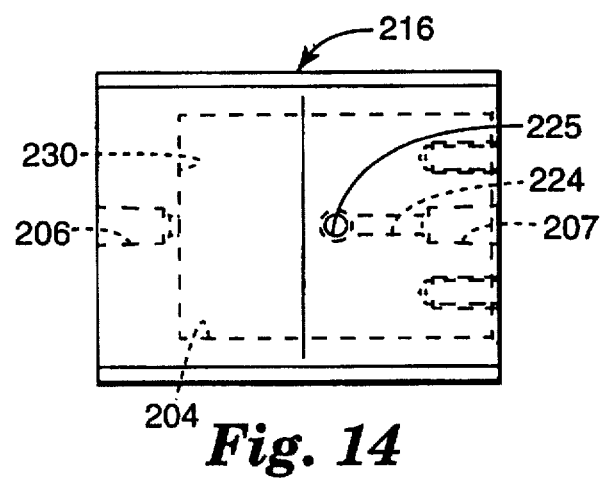
FIG. 14 is a bottom plan view of the housing of FIG. 13 illustrating passageways and the inflation chamber in phantom.
Figure 15:
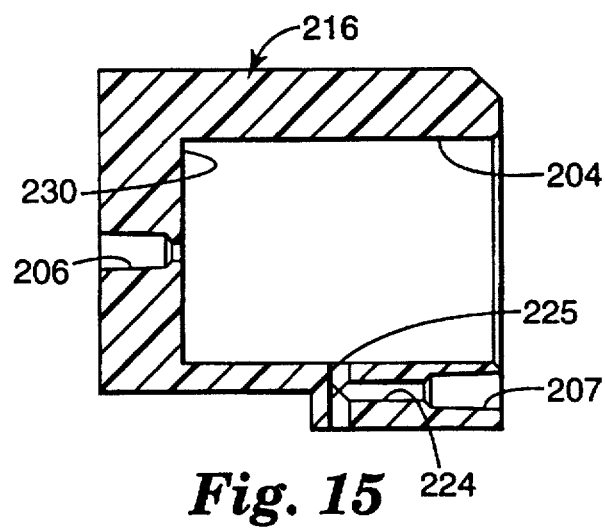
FIG. 15 is a cross-sectional view substantially along line 15—15 of FIG. 13.
Figure 16:
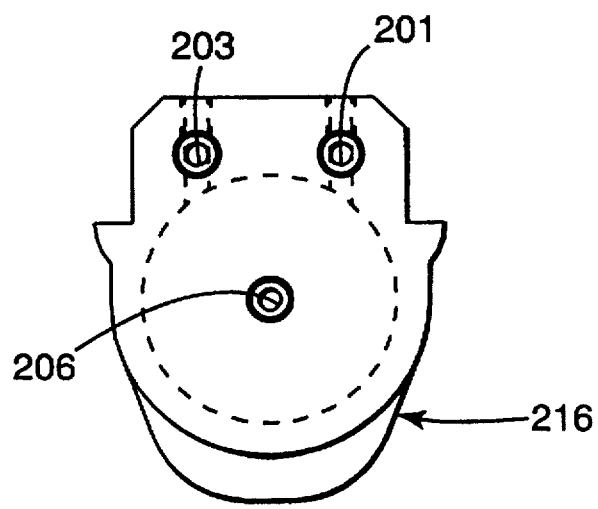
FIG. 16 is a left end view of the housing of FIGS. 13-15.
Figure 17:
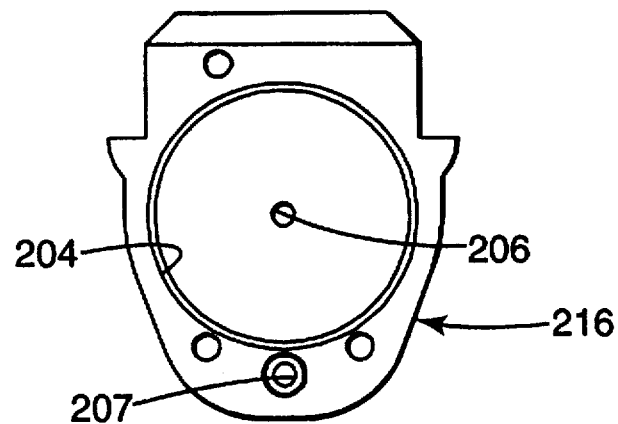
FIG. 17 is a right end view of the housing of FIGS. 13-16.

As illustrated in FIGS. 13 and 14, the valve means 210 further comprises (1) a cardioplegia supply passageway 224 having an opening 225 through the wall defining the inflation chamber 204; (2) an antegrade passageway 226 having an opening 227 through the wall defining the inflation chamber 204; and (3) a retrograde passageway 228 having an opening 229 through the wall defining the inflation chamber 204. The cardioplegia supply passageway 224 constitutes part of the cardioplegia supply port 207 and thus is in fluid communication with the cardioplegia supply tubing 48. The antegrade passageway 226 constitutes part of the antegrade port 201 and thus is in fluid communication with the antegrade tubing 23. The retrograde passageway 228 constitutes part of the retrograde port 203 and thus is in fluid communication with the retrograde tubing 38.

As best illustrated in FIG. 13, the openings 225, 227 and 229 of the cardioplegia supply passageway 224, antegrade passageway 226 and retrograde passageway 228 are offset from one another longitudinally along the inflation chamber 204. The openings 225, 227 and 229 are preferably also offset radially as shown in FIG. 13. The opening 225 of the cardioplegia supply passageway 224 is positioned in the axial direction between the openings 227 and 229 of the antegrade and retrograde passageways 226 and 228. The opening 229 of the retrograde passageway 228 is closer to the end 230 of the inflation chamber 204 through which the inflation port 206 opens. The opening 227 of the antegrade passageway 226 is farther from the end 230 of the inflation chamber 204 through which the inflation port 206 opens.

As a result of the arrangement of the openings 225, 227 and 229 shown in FIG. 13, when the piston 208 moves to its first position (FIG. 8), which is spaced away from the inflation port 206, the valve passageway 222 brings the antegrade passageway 226 and cardioplegia supply passageway 225 but not the retrograde passageway 228 into fluid communication. This allows cardioplegia solution to be provided through the switch 200 and antegrade tubing 23 to the antegrade cardioplegia catheter 22. When the piston 208 moves to its second position (FIG. 9), which is relatively close to the inflation port 206, the valve passageway 222 brings the retrograde passageway 228 and cardioplegia supply passageway 224 but not the antegrade passageway 226 into fluid communication. This allows cardioplegia solution to be provided through the switch 200 and retrograde tubing 38 to the infusion lumen of the retrograde catheter 24.

Also, as a result of this arrangement, the forward sealing rings 212 of the piston 208 prevent fluid communication between the retrograde passageway 228 and the cardioplegia supply passageway 224 when the piston 208 is in its first position (FIG. 8), and the rearward sealing rings 214 of the piston 208 prevent fluid communication between the antegrade passageway 226 and the cardioplegia supply passageway 224 when the piston 208 is in its second position (FIG. 9).

Figure 7:
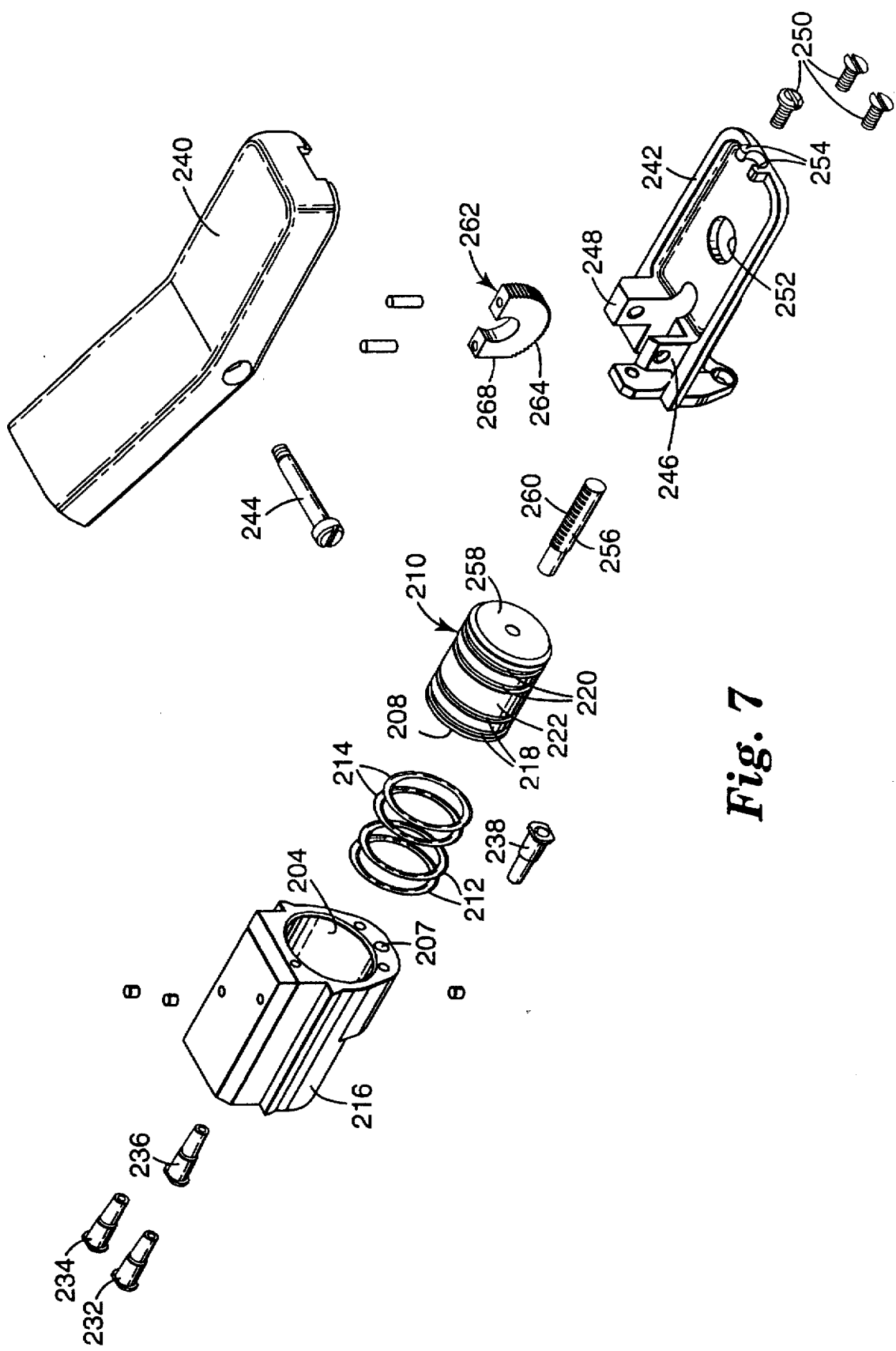
FIG. 7 is an exploded view of the antegrade/retrograde switch of FIGS. 5 and 6.
Figure 8:
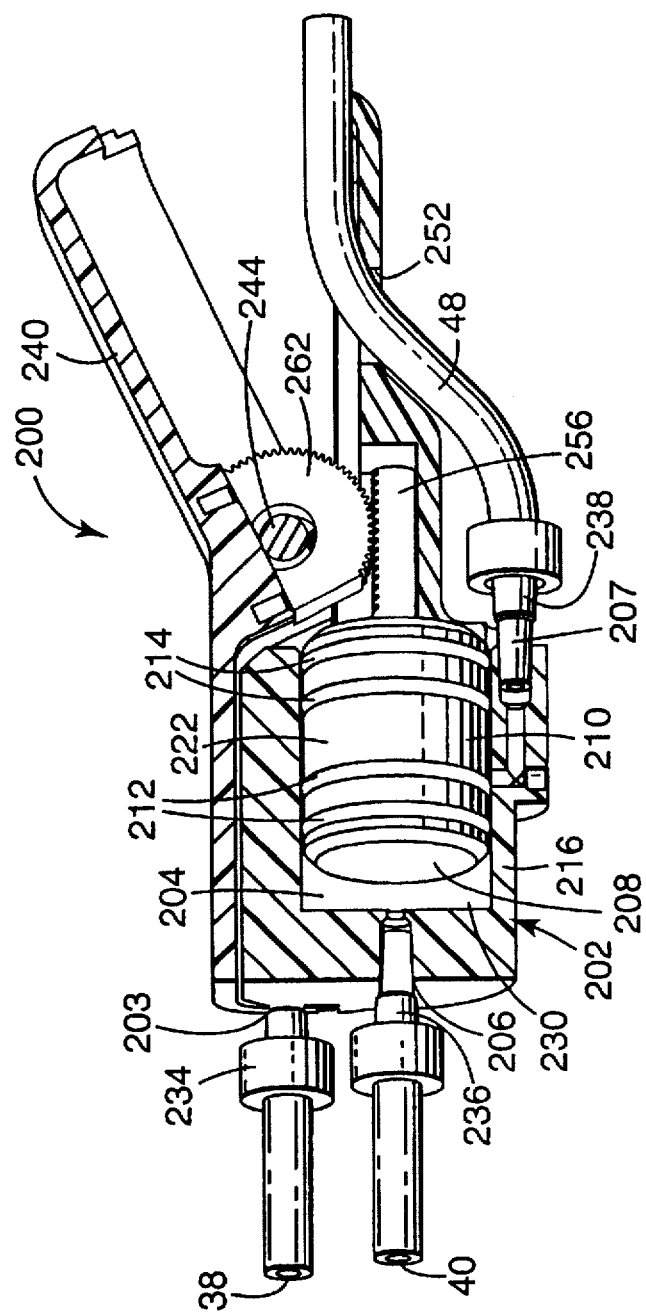
FIG. 8 is a cross-sectional view of the antegrade/retrograde switch of FIGS. 5-7, illustrating a first position in which cardioplegia solution is directed to an antegrade catheter and the retention balloon of a retrograde catheter is deflated.

As illustrated in FIG. 7, connection means or connectors 232, 234, 236 and 238 are mounted in antegrade port 201, retrograde port 203, balloon inflation port 206 and cardioplegia supply port 207 for connecting tubing 23, 38, 40 and 48, respectively, to the ports 201, 203, 206 and 207. Connectors 232, 234, 236 and 238 may take any suitable form, including conventional luer ports 232, 234, 236 and 238 for releasable connecting luer fittings (not shown) on tubing 23, 38, 40 and 48. Alternatively, the switch 200 may be provided with the tubing 23, 38, 40 and 48 solvent bonded or otherwise bonded to their respective ports 201, 203, 206 and 207.

As illustrated in FIGS. 5–9, a lever 240 is pivotably mounted on a frame 242, which is mounted on the switch housing 216. The lever 240 is adapted for pivotable movement between a first position (FIG. 8) and a second position (FIG. 9) corresponding to the first and second positions of the piston 208. The lever 240 is operatively connected to the piston 208 to move the piston 208 between its first and second positions.

The lever 240 is conveniently mounted for pivotable movement relative to the frame 242 by a pin 244 received in mounting blocks 246 and 248 on the frame 242. The lever 240 preferably has two sections provided at an angle of approximately 150 degrees relative to one another to allow pivoting relative the frame 242 and switch housing 216. The frame 242 is conveniently mounted on the switch housing 216 by three screws 250. Most preferably, the frame 242 includes an opening 252 and arcuate arms 254 for receiving and holding the cardioplegia supply tubing 48. The arcuate arms 254 are spaced to closely frictionally receive the cardioplegia supply tubing 248 to hold the tubing 248.

Most preferably, the lever 240 includes an opening (not shown) that is aligned with a symbol (not shown) on the switch housing 216 when the lever 240 is moved to its second position, indicating that the switch 200 is providing cardioplegia solution to the retrograde catheter 24.

Figure 10:
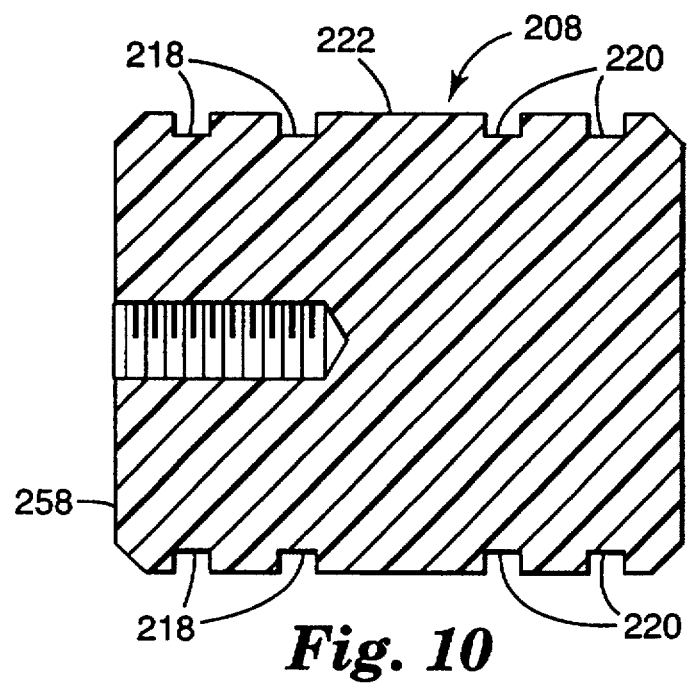
FIG. 10 is a cross-sectional view through a piston of the antegrade/retrograde switch of FIGS. 5-9.
Figure 11:
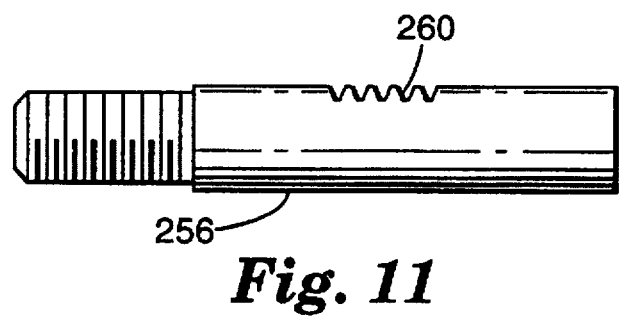
FIG. 11 is a side view of a piston rod of the antegrade/retrograde switch of FIGS. 5-10, illustrating a rack portion having teeth.
Figure 12:
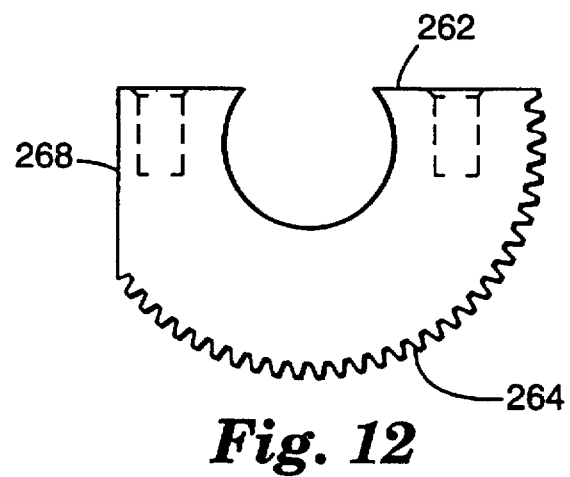
FIG. 12 is a side elevational view of a pinion gear of the antegrade/retrograde switch of FIGS. 5-11, illustrating teeth that are adapted for intermeshing engagement with the teeth of the rack portion of the piston rod.

As illustrated in FIGS. 7, 10 and 11, the piston 208 is provided with a piston rod 256 extending rearwardly from the rear surface 258 of the piston 208. The piston rod 256 has a rack portion 260 with teeth to form the rack portion 260 of a rack-and-pinion linkage. A pinion 262 (FIGS. 7–9 and 12) is mounted on the lever 240, and the pinion 262 has teeth 264 in intermeshing engagement with the teeth of the rack portion 260 of the piston rod 256 to move the piston 208 as the lever 240 is pivoted.

Alternatively, additional passageways could be provided in a switch similar to switch 200 to provide simultaneous switching between pressure sensing lumens of the antegrade and retrograde catheters. Such passageways, which are not shown in the drawing, could include (a) a second valve passageway in the piston; (b) an antegrade pressure sensing passageway adapted to be connected in fluid communication with a pressure sensing lumen of the antegrade catheter; (c) a retrograde pressure sensing passageway adapted to be connected in fluid communication with a pressure sensing lumen of the retrograde catheter; and (d) another pressure sensing passageway adapted to be connected with a pressure sensor. The second valve passageway would bring the antegrade pressure sensing passageway into fluid communication with the pressure sensor when the piston is in its first position, in which cardioplegia solution is provided to the antegrade catheter. The second valve passageway would bring the retrograde pressure sensing passageway into fluid communication with the pressure sensor when the piston is in its second position, in which the retention balloon of the retrograde catheter is inflated and cardioplegia solution is provided to the retrograde catheter.

Figure 18:
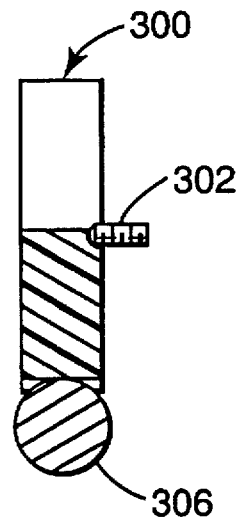
FIG. 18 is a diagrammatic view of a pinion gear, rack portion of a piston rod and detent mechanism of another embodiment of the antegrade/retrograde switch of the invention.
Figure 19:
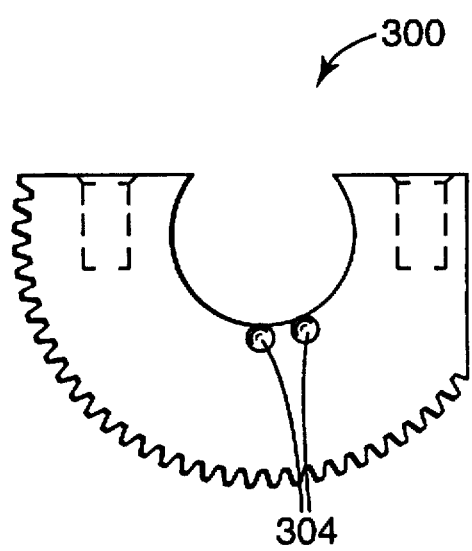
FIG. 19 is a side view of the pinion gear of FIG. 18, illustrating detent depressions for receiving a spring-loaded detent ball mechanism.

FIGS. 18 and 19 illustrate an alternative embodiment of the invention identical to the switch 200 of FIGS. 5–17, except that a detent mechanism is provided for retaining the piston in its first and second positions. The detent mechanism includes a pinion gear 300 similar to pinion 262 and a spring-loaded detent ball mechanism 302 that engages detent depressions 304 in the pinion gear 300 to releasably lock the pinion gear 300, and thus the piston rod 306, in either the first or second positions.

It will be appreciated that either switch 100 or switch 200 could be modified to alternatively inflate balloons in both first and second catheters when fluid is being provided to that catheter. Such a modification could involve (a) adding an additional plunger to a switch similar to switch 100 for inflating the second balloon, (b) adding an additional piston into a switch similar to switch 200 for inflating the second balloon, or (c) arranging a single plunger or piston to alternatively inflate two different balloons when the piston or plunger is moved between a first and second position, for example, by providing a second inflation chamber defined by the back side of the piston or plunger.

OPERATION

The switches 100 and 200 are adapted for use in administering cardioplegia solution selectively in the antegrade direction via the arterial system of a patient's heart and in the retrograde direction via the venous system of the patient's heart.

The switch 100 or 200 could be packaged in a preprimed condition, primed for example with saline solution, or the switch 100 or 200 and tubing 23, 38, 40 and 48 could be primed by the perfusionist or other medical personnel. In order to prime the switch 100 or 200, the switch 100 or 200 would first (for example) be primed with the piston 208 or plungers 108, 114 in their first position to prime the antegrade passageways, ports and tubing, and then the piston 208 or plungers 108, 114 would be moved to their second position to prime the retrograde passageways, ports and tubing. The cardioplegia supply tubing 48 and cardioplegia supply port and passageways would be primed in the first step of the above priming process.

In operation, the distal end of the retrograde coronary sinus catheter 24 is inserted into a patient's coronary sinus. As discussed above, the coronary sinus catheter 24 includes an infusion lumen for supplying cardioplegia solution to a patient's heart, an inflatable retention balloon 26 for engaging the walls of the coronary sinus to retain the catheter 24 in position, and a balloon inflation lumen, separate from the infusion lumen, for inflating the inflatable retention balloon 26.

The distal end of the antegrade catheter 22 is inserted into a coronary artery, for example, the aortic root. As discussed above, the antegrade catheter 22 includes an infusion lumen for supplying cardioplegia solution to a patient's heart.

A source 42, 44 and 46 of cardioplegia solution is provided.

The antegrade/retrograde switch 100 or 200 is connected via tubing 23, 38, 40 and 48 to the retrograde catheter 24, the antegrade catheter 22 and the source of cardioplegia solution. As discussed above, the antegrade/retrograde switch 100 or 200 includes valve means 110 or 210 and balloon inflation means 102 or 202. The valve means 110 or 210 is adapted for selectively directing cardioplegia solution supplied to switch 100 or 200 from the source of cardioplegia solution to the infusion lumen of either of the retrograde coronary sinus catheter 24 and the antegrade catheter 22. The balloon inflation means 102 or 202 is adapted for inflating the retention balloon 26 of the coronary sinus catheter 24 with fluid via the balloon inflation lumen when the valve means 110 or 210 directs cardioplegia solution to the infusion lumen of the retrograde coronary sinus catheter 24 and for deflating the retention balloon 26 via the balloon inflation lumen when the valve means 110 or 210 directs cardioplegia solution to the infusion lumen of the antegrade catheter 22.

The valve means 110 or 210 may be actuated to direct cardioplegia solution to the antegrade catheter 22 with the retention balloon 26 of the retrograde catheter 24 deflated by the balloon inflation means 102 or 202 of the switch 100 or 200. For example, as the handle 118 of switch 100 is pulled to its first position (FIG. 3), fluid is drawn into the balloon inflation chamber 104 with the plunger 108 to deflate the retention balloon 26 of the retrograde catheter 24, and the valve member 116 being pulled to its first position between the cardioplegia supply inlet 107 and the retrograde outlet 103, thereby directing cardioplegia solution from the cardioplegia supply inlet 107 to the antegrade outlet 101. As a second example, when the lever 240 of switch 200 is pivoted to its first position (FIG. 8), the piston 208 is pulled to its first position spaced from the inflation port 206 to draw fluid into the inflation chamber 204 and deflate the retention balloon 26 of the retrograde catheter 24 and to align the valve passageway 222 defined by the piston 208 with the antegrade opening 227 and cardioplegia supply opening 225, thereby allowing cardioplegia solution to flow from the source of cardioplegia solution through the switch 200 to the antegrade catheter 22.

The valve means 110 or 210 may also be actuated to direct cardioplegia solution to the infusion lumen of the retrograde catheter 24 with the balloon inflation means 102 or 202 inflating the retention balloon 26 via the balloon inflation lumen to help retain the retrograde catheter 24 in position in the coronary sinus. For example, when the handle 118 of the switch 100 is pushed to its second position (FIG. 4), the first plunger 108 moves to its second position expelling fluid from the inflation chamber 104 to inflate the retention balloon 26 of the retrograde catheter 24, and the second plunger 116 moves to its second position between the cardioplegia supply inlet 107 and the antegrade outlet 101, thereby blocking flow through the antegrade outlet 101 while permitting flow through the retrograde outlet 103. As a second example, when the lever 240 of switch 200 is moved to its second position (FIG. 9), the piston 208 is moved to its second position expelling fluid from the inflation chamber 204 to inflate the retention balloon 26 of the retrograde catheter 24, and aligning the valve passageway 222 defined by the piston 208 with the cardioplegia supply opening 225 and the retrograde opening 229, thereby directing cardioplegia solution to the retrograde catheter.

In either example, the second position (FIGS. 4 and 9) may include a range of positions that the first plunger 108 and piston 208 may be in to adjustably inflate the retention balloon 26 of the retrograde catheter 24 while the second plunger 116 or valve passageway 222 directs cardioplegia solution to the retrograde catheter 24. The surgeon retains the ability to control inflation of the retention balloon 26 of the retrograde catheter 24.

It is possible to set up the cardioplegia circuit so that the first plunger 108 or piston 208 actually provide suction or vacuum when in their first position to pull the retention balloon 26 inwardly. This may be desirable to facilitate introducing the distal end of the retrograde catheter 24 into the coronary sinus. This may be accomplished by connecting the balloon inflation tubing 40 to the retrograde catheter 24 and the inflation port 106 or 206 with the first plunger 108 or piston 208 in an intermediate position between its first and second positions, and then pulling the first plunger 108 or piston 208 to its first position to draw a vacuum. As used herein, the term "vacuum" merely refers to the pressure in the interior of the retention balloon 26 being less than outside ambient pressure or local environmental pressure (e.g., pressure in the right atrium or coronary sinus). The term "vacuum" is used to refer to the interior pressure of the balloon 26 being sufficiently low that the balloon 26 is drawn toward the catheter tube.

As various changes could be made in the above constructions and methods without departing from the scope of the invention as specified in the claims, it is intended that all matter contained in the description above or shown in the accompanying drawing shall be interpreted as illustrative and not in a limiting sense.

We claim:

1. A method of administering cardioplegia solution selectively in the antegrade direction via the arterial system of a patient's heart and in the retrograde direction via the venous system of the patient's heart, the method comprising the steps of:

inserting a retrograde coronary sinus catheter into a patient's coronary sinus, the coronary sinus catheter including an infusion lumen for supplying cardioplegia solution to a patient's heart, an inflatable retention balloon for engaging the walls of the coronary sinus to retain the catheter in position, and a balloon inflation lumen, separate from the infusion lumen, for inflating the inflatable retention balloon;

inserting an antegrade catheter into a coronary artery, the antegrade catheter including an infusion lumen for supplying cardioplegia solution to a patient's heart;

providing a source of cardioplegia solution;

connecting an antegrade/retrograde switch via tubing to the retrograde coronary sinus catheter, the antegrade catheter and the source of cardioplegia solution, the antegrade/retrograde switch including valve means for selectively directing cardioplegia solution supplied to the switch from the source of cardioplegia solution to the infusion lumen of either of the retrograde coronary sinus catheter and the antegrade catheter, and balloon inflation means for inflating the retention balloon of the coronary sinus catheter with fluid via the balloon inflation lumen when the valve means directs cardioplegia solution to the infusion lumen of the retrograde coronary sinus catheter and for deflating the retention balloon via the balloon inflation lumen when the valve means directs cardioplegia solution to the infusion lumen of the antegrade catheter;

actuating the valve means to direct cardioplegia solution to the antegrade catheter with the retention balloon of the retrograde catheter deflated by the balloon inflation means of the switch; and actuating the valve means to direct cardioplegia solution to infusion lumen of the retrograde catheter with the balloon inflation means inflating the retention balloon via the balloon inflation lumen to help retain the retrograde catheter in position in the coronary sinus.

2. An antegrade/retrograde switch for selectively directing cardioplegia solution to either one of an antegrade cardioplegia catheter and a retrograde coronary sinus catheter having a manually inflatable balloon in order to selectively administer cardioplegia solution to a patient's heart in antegrade or retrograde directions, the switch comprising:

balloon inflation means for inflating the balloon of the retrograde coronary sinus catheter, the balloon inflation means comprising an inflation chamber for fluid, a port into the chamber for bringing the inflation chamber into fluid communication with the manually inflatable balloon of the retrograde coronary sinus catheter, and actuating means selectively operable for driving fluid out of the inflation chamber through the port, whereby fluid is driven into the balloon of the retrograde coronary sinus catheter to inflate the balloon, and for drawing fluid through the port into the inflation chamber, whereby fluid is drawn out of the balloon of the retrograde coronary sinus catheter into the inflation chamber to deflate the balloon;

a cardioplegia supply passageway for receiving cardioplegia solution from a source of cardioplegia solution;

valve means for selectively directing cardioplegia solution from the cardioplegia supply passageway to either one of the antegrade catheter and the retrograde; and means for operatively connecting the actuating means and the valve means such that, when the actuating means inflates the balloon of the retrograde catheter, the valve means directs cardioplegia solution to the retrograde catheter, and, when the actuating means deflates the balloon of the retrograde catheter, the valve means directs cardioplegia solution to the antegrade catheter.

3. An antegrade/retrograde switch according to claim 2 wherein the actuating means is movable within the inflation chamber between a first position, wherein the fluid is within the inflation chamber and the balloon is deflated, and a second position, wherein fluid has been driven out of the inflation chamber by the actuating means to inflate the balloon.

4. An antegrade/retrograde switch according to claim 3 wherein the actuating means comprises a piston slidingly received in the inflation chamber in sealing engagement with walls defining the inflation chamber, the means for operatively connecting the actuating means and the valve means comprising the valve means being provided in the piston and the walls defining the inflation chamber.

5. An antegrade/retrograde switch according to claim 4 further comprising a switch housing having the walls defining the inflation chamber, the piston having side walls generally adjacent the walls defining the inflation chamber and movable therealong, the valve means comprising:

a retrograde passageway through the wall defining the inflation chamber, the retrograde passageway including a first connector for connecting tubing in fluid communication with the retrograde passageway to provide cardioplegia solution to the retrograde catheter;

an antegrade passageway through the wall defining the inflation chamber, the antegrade passageway including a second connector for connecting tubing in fluid communication with the antegrade passageway to provide cardioplegia solution to the antegrade catheter;

the cardioplegia supply passageway passing through the wall defining the inflation chamber, the cardioplegia supply passageway including a third connector for connecting tubing in fluid communication with the cardioplegia supply passageway to provide cardioplegia solution to the cardioplegia supply passageway; and a valve passageway defined by the piston, the valve passageway bringing the cardioplegia supply passageway and antegrade passageway into fluid communication when the piston is in its first position, and the valve passageway bringing the cardioplegia supply passageway and retrograde passageway into fluid communication when the piston is in its second position.

6. An antegrade/retrograde switch according to claim 5 wherein the piston prevents fluid communication between the retrograde passageway and cardioplegia supply passageway when the piston is in its first position, and the piston prevents fluid communication between the antegrade passageway and the cardioplegia supply passageway when the piston is in its second position.

7. An antegrade/retrograde switch according to claim 6 further comprising a lever pivotable mounted on the switch housing and operatively connected to the piston to move the piston between its first and second positions.

8. An antegrade/retrograde switch according to claim 7 further comprising a rod extending from the piston and having a rack portion with teeth, and a pinion on the lever, the pinion having teeth in intermeshing engagement with the teeth of the rack portion of the rod to move the piston as the lever is pivoted.

9. An antegrade/retrograde switch according to claim 8 wherein the piston has a circumference and at least two annular sealing rings extending along the circumference of the piston and defining the valve passageway along the circumference of the piston between the two annular sealing rings.

10. An antegrade/retrograde switch according to claim 5 further comprising means for releasably retaining the piston in its first and second positions.

11. An antegrade/retrograde switch according to claim 3 wherein the balloon inflation means comprises a syringe defining the inflation chamber and having a plunger, constituting the actuating means, movable within the inflation chamber for pressurizing and depressurizing the balloon.

12. An antegrade/retrograde switch according to claim 3 wherein the valve means comprises:

a valve chamber having an inlet, a retrograde outlet adapted to be in fluid communication with the retrograde catheter, and an antegrade outlet adapted to be in fluid communication with the antegrade catheter; and a valve member movable within the valve chamber between a first position, wherein the antegrade outlet is in fluid communication with the inlet of the valve chamber and the retrograde outlet is blocked, and a second position, wherein the retrograde outlet is in fluid communication with the inlet of the valve chamber and the antegrade outlet is blocked;

the actuating means and the valve member being operatively connected such that the valve member is in its first position when the actuating means is in its first position and the valve member is in its second position when the actuating means is in its second position.

13. An antegrade/retrograde switch according to claim 12 wherein the actuating means comprises a first plunger movable within the inflation chamber along a first longitudinal axis of motion between its first and second positions, and the valve member comprises a second plunger movable within the valve chamber along a second longitudinal axis of motion generally parallel with the first longitudinal axis of motion between its first and second positions in generally the same direction as the first plunger;

the first and second plungers being connected such that the first and second plungers are simultaneously moved in generally the same direction between the first and second positions.

14. An antegrade/retrograde switch according to claim 13 wherein the means for operatively connecting the actuating means and the valve means comprises a handle, operatively linking the first and second plungers, for manually and simultaneously moving the first and second plungers between their first and second positions.

15. An antegrade/retrograde switch according to claim 12 wherein:

the balloon inflation means further comprises a first housing defining the inflation chamber as being generally elongate having a longitudinal axis coaxial with the first longitudinal axis of motion of the first plunger;

the valve means further comprises a valve housing defining the valve chamber as being generally elongate having a longitudinal axis coaxial with the second longitudinal axis of motion of the second plunger and generally parallel with the longitudinal axis of the inflation chamber, the valve chamber having opposite ends; and the retrograde and antegrade outlets being located generally adjacent the opposite ends of the valve chamber relative to one another, and the inlet being located generally between the retrograde and antegrade outlets, the second plunger when in its first position being positioned between the inlet and the retrograde outlet to block passage of cardioplegia solution through the retrograde outlet, and the second plunger when in its second position being positioned between the inlet and the antegrade outlet to block passage of cardioplegia solution through the antegrade outlet.

16. An antegrade/retrograde switch according to claim 15 wherein the inflation chamber has opposite ends generally adjacent the opposite ends of the valve chamber, the opposite ends of each of the inflation and valve chambers comprising:

a first end, with the handle extending outwardly from the first ends of the inflation and valve chambers, the retrograde outlet of the valve chamber being generally adjacent the first end of the valve chamber; and a second end, with the port of the inflation chamber extending from the second end, the antegrade outlet of the valve chamber being generally adjacent the second end of the valve chamber.

17. An antegrade/retrograde switch according to claim 16 wherein the inflation chamber is defined by a generally cylindrical internal wall of the first housing, and the valve chamber is defined by a generally cylindrical internal wall of the valve housing, the first and second plungers comprising elastomeric sealing members in sealing engagement with the internal walls defining the inflation chamber and the valve chamber, respectively.

18. An antegrade/retrograde switch according to claim 16 wherein the first housing and valve housing are integrally molded in one piece.

19. An antegrade/retrograde switch according to claim 18 wherein the port, inlet, antegrade outlet and retrograde outlet each further comprise connection means for connecting with tubing in fluid communication with the balloon of the retrograde catheter, the source of cardioplegia solution, an infusion lumen of the antegrade catheter and an infusion lumen of the retrograde catheter, respectively.

20. An antegrade/retrograde switch for selectively directing cardioplegia solution to either one of an antegrade cardioplegia catheter and a retrograde coronary sinus catheter having a manually inflatable balloon in order to selectively administer cardioplegia solution to a patient's heart in the antegrade or retrograde directions, the switch comprising:

a housing having internal walls defining an inflation chamber and a valve chamber, the housing having:

a port into the inflation chamber and a first connector on the port for connecting tubing in fluid communication with a balloon of a retrograde catheter;

an inlet into the valve chamber and a second connector on the inlet for connecting tubing in fluid communication with a source of cardioplegia solution;

a retrograde outlet from the valve chamber and a third connector on the retrograde outlet for connecting tubing in fluid communication with an infusion lumen of a retrograde catheter; and an antegrade outlet from the valve chamber and a fourth connector on the antegrade outlet for connecting tubing in fluid communication with an infusion lumen of an antegrade catheter; and an actuator member in the inflation chamber in sealing engagement with the walls of the housing defining the inflation chamber; and a valve member in the valve chamber in sealing engagement with the walls of the housing defining the valve chamber;

the actuator member and valve member being operatively linked for movement between:

a first position, wherein the actuator member is spaced from the port of the inflation chamber whereby the balloon of the retrograde catheter is deflated, and the valve member is positioned between the inlet and the retrograde outlet to direct cardioplegia solution from the inlet through the antegrade outlet; and a second position, wherein the actuating member is closer to the port of the inflation chamber than in the first position whereby the balloon of the retrograde catheter is inflated, and the valve member is positioned between the inlet and the antegrade outlet to direct cardioplegia solution from the inlet through the retrograde outlet.

21. An antegrade/retrograde switch according to claim 20 further comprising a single handle, operatively linked with the actuating member and valve member, for manually moving the actuating member and valve member between their first and second positions.

22. An antegrade/retrograde switch according to claim 21 wherein the internal walls defining the inflation chamber and valve chamber are each generally cylindrical, the actuating member and valve member each including generally circular elastomeric sealing means in sealing engagement with the internal walls defining the inflation chamber and valve chamber, respectively.

23. An antegrade/retrograde switch according to claim 22 wherein actuating member and valve member each further include a rod linking the actuating member and valve member, respectively, with the single handle.

24. An antegrade/retrograde switch according to claim 23 wherein the housing is integrally molded of synthetic resin material.

25. An antegrade/retrograde switch according to claim 23 wherein:

the inflation chamber is generally elongate having a longitudinal axis, the actuating member moving between the first and second positions along a first longitudinal axis of motion coaxial with the longitudinal axis of the inflation chamber;

the valve chamber is generally elongate having a longitudinal axis, the valve member moving between the first and second positions along a second longitudinal axis of motion coaxial with the longitudinal axis of the valve chamber and generally parallel with the longitudinal axis of the inflation chamber, the valve chamber having opposite ends; and the retrograde and antegrade outlets being located generally adjacent the opposite ends of the valve chamber relative to one another, and the inlet being located generally between the retrograde and antegrade outlets, the valve member when in the first position being positioned between the inlet and the retrograde outlet to block passage of cardioplegia solution through the retrograde outlet, and the valve member when in the second position being positioned between the inlet and the antegrade outlet to block passage of cardioplegia solution through the antegrade outlet.

26. An antegrade/retrograde switch according to claim 25 wherein the inflation chamber has opposite ends generally adjacent the opposite ends of the valve chamber, the opposite ends of each of the inflation chamber and valve chamber comprising:

a first end, with the rods extending outwardly from the first ends of the inflation and valve chambers to the single handle, the retrograde outlet of the valve chamber being generally adjacent the first end of the valve chamber; and a second end, with the port of the inflation chamber extending from the second end of the inflation chamber, the antegrade outlet of the valve chamber being generally adjacent the second end of the valve chamber.

27. An antegrade/retrograde switch for selectively directing cardioplegia solution to either one of an antegrade cardioplegia catheter and a retrograde coronary sinus catheter having a manually inflatable balloon in order to selectively administer cardioplegia solution to a patient's heart in antegrade or retrograde directions, the switch comprising:

a switch housing having internal walls defining an inflation chamber for fluid;

a port into the inflation chamber for bringing the inflation chamber into fluid communication with the manually inflatable balloon of the retrograde coronary sinus catheter;

a piston in sealing engagement with the internal walls defining the inflation chamber, the piston being selectively movable within the inflation chamber from a first position to a second position for driving fluid out of the inflation chamber through the port, whereby fluid is driven into the balloon of the retrograde coronary sinus catheter to inflate the balloon, and the piston being selectively movable from the second position to the first position for drawing fluid through the port into the inflation chamber, whereby fluid is drawn out of the balloon of the retrograde coronary sinus catheter into the inflation chamber to deflate the balloon;

a retrograde passageway through the internal wall defining the inflation chamber, the retrograde passageway including a first connector for connecting tubing in fluid communication with the retrograde passageway to provide cardioplegia solution to the retrograde catheter;

an antegrade passageway through the internal wall defining the inflation chamber, the antegrade passageway including a second connector for connecting tubing in fluid communication with the antegrade passageway to provide cardioplegia solution to the antegrade catheter;

a cardioplegia supply passageway through the internal wall defining the inflation chamber, the cardioplegia supply passageway including a third connector for connecting tubing in fluid communication with the cardioplegia supply passageway to provide cardioplegia solution to the cardioplegia supply passageway; and a valve passageway defined by the piston, the valve passageway bringing the cardioplegia supply passageway and antegrade passageway into fluid communication when the piston is in its first position, and the valve passageway bringing the cardioplegia supply passageway and retrograde passageway into fluid communication when the piston is in its second position, whereby:

when the piston inflates the balloon of the retrograde catheter, the valve passageway directs cardioplegia solution to the retrograde catheter; and when the piston deflates the balloon of the retrograde catheter, the valve passageway directs cardioplegia solution to the antegrade catheter.

28. An antegrade/retrograde switch according to claim 27 wherein the piston prevents fluid communication between the retrograde passageway and cardioplegia supply passageway when the piston is in its first position, and the piston prevents fluid communication between the antegrade passageway and the cardioplegia supply passageway when the piston is in its second position.

29. An antegrade/retrograde switch according to claim 28 further comprising a lever pivotable mounted on the switch housing and operatively connected to the piston to move the piston between its first and second positions.

30. An antegrade/retrograde switch according to claim 29 further comprising a rod extending from the piston and having a rack portion with teeth, and a pinion on the lever, the pinion having teeth in intermeshing engagement with the teeth of the rack portion of the rod to move the piston as the lever is pivoted.

31. An antegrade/retrograde switch according to claim 30 wherein the piston has a circumference and at least two annular sealing rings extending along the circumference of the piston and defining the valve passageway along the circumference of the piston between the two annular sealing rings.

32. An antegrade/retrograde switch according to claim 27 further comprising means for releasably retaining the piston in its first and second positions.

33. A switch for selectively directing a first fluid to either one of a first catheter and a second catheter, the second catheter being of the type including an infusion lumen, an inflatable balloon and a balloon inflation lumen, separate from the infusion lumen, for inflating and deflating the balloon, the switch comprising:

a housing having first, second, third and fourth ports, the first port being adapted to be connected in fluid communication with the first catheter, the second port being adapted to be connected in fluid communication with the infusion lumen of the second catheter, the third port being adapted to be connected in fluid communication with a source of the first fluid, and the fourth port being adapted to be connected in fluid communication with the balloon inflation lumen of the second catheter;

valve means for selectively directing fluid from the source of the first fluid to the first and second catheters, the valve means including a valve member movable within the housing between (1) a first position, in which the valve means brings the first and third ports but not the second port into fluid communication with each other, whereby the first fluid is directed from the source of the first fluid to the first catheter, and (2) a second position, in which the valve means brings the second and third ports but not the first port into fluid communication with each other, whereby the first fluid is directed from the source of the first fluid to the second catheter; and balloon inflation means, within the housing and operatively linked with the valve means, for expelling a second fluid out through the fourth port when the valve member of the valve means is moved to its second position and for drawing the second fluid in through the fourth port when the valve member of the valve means is moved to its first position, whereby the balloon of the second catheter is deflated when the first fluid is directed to the first catheter and the balloon of the second catheter is inflated with the second fluid when the first fluid is directed to the second catheter.

34. A switch according to claim 33 wherein the balloon inflation means comprises an inflation chamber within the housing in fluid communication with the fourth port, and a piston movable within the inflation chamber to expel the second fluid through the fourth port and to draw in the second fluid through the fourth port.

35. A switch according to claim 34 wherein the valve member is integrally provided in the piston.

36. A switch according to claim 34 wherein the valve means comprises a valve chamber within the housing and separate from the inflation chamber, the valve member being movable within the valve chamber between the first and second positions, the valve member and piston being operatively connected for simultaneous movement, the switch further comprising a handle for moving the valve member and piston.

37. A cardioplegia administration system for selectively administering cardioplegia solution to a patient's heart in the antegrade direction via the arterial system of the heart or in the retrograde direction via the venous system of the heart, the system comprising:

an antegrade catheter having an infusion lumen for administering cardioplegia solution to a patient's heart via the arterial system of the heart in the antegrade direction;

antegrade tubing in fluid communication with the infusion lumen of the antegrade catheter for providing cardioplegia solution to the infusion lumen of the antegrade catheter;

a retrograde catheter having an infusion lumen for administering cardioplegia solution to a patient's heart via the venous system of the heart in the retrograde direction, an inflatable retention balloon for retaining the retrograde catheter in position in the patient's heart, and an inflation lumen in fluid communication with the balloon for providing fluid to the balloon to inflate the balloon and for draining fluid from the balloon to deflate the balloon;

retrograde tubing in fluid communication with the infusion lumen of the retrograde catheter for providing cardioplegia solution to the infusion lumen of the retrograde catheter;

balloon-inflation tubing in fluid communication with the inflation lumen of the retrograde catheter for supplying and draining fluid to and from the retention balloon to inflate and deflate the retention balloon;

a source of cardioplegia solution;

cardioplegia supply tubing in fluid communication with the source of cardioplegia solution; and an antegrade/retrograde switch for selectively directing cardioplegia solution to either one of the antegrade and retrograde catheters, the switch comprising:

balloon inflation means for inflating the balloon of the retrograde coronary sinus catheter, the balloon inflation means comprising an inflation chamber for fluid, a port into the inflation chamber in fluid communication with balloon-inflation tubing and the retention balloon of the retrograde catheter, and actuating means selectively operable for driving fluid out of the inflation chamber through the port and via the balloon-inflation tubing and inflation lumen into the retention balloon to inflate the retention balloon, and for drawing fluid from the retention balloon through the inflation lumen, balloon-inflation tubing, and port into the inflation chamber to deflate the retention balloon; and valve means, in fluid communication with the antegrade tubing, the retrograde tubing and the cardioplegia supply tubing, for selectively directing cardioplegia solution from the cardioplegia supply tubing and source of cardioplegia solution to either one of the antegrade and retrograde catheters via the respective antegrade tubing and retrograde tubing;

means for operatively connecting the actuating means and the valve means such that, when the actuating means inflates the balloon of the retrograde catheter, the valve means directs cardioplegia solution to the retrograde catheter, and, when the actuating means deflates the balloon of the retrograde catheter, the valve means directs cardioplegia solution to the antegrade catheter.

38. A cardioplegia administration system according to claim 37 wherein the actuating means of the switch is movable within the inflation chamber between a first position, wherein the fluid is within the inflation chamber and the retention balloon of the retrograde catheter is deflated, and a second position, wherein fluid has been driven out of the inflation chamber by the actuating means to inflate the retention balloon of the retrograde catheter.

39. A cardioplegia administration system according to claim 38 wherein the actuating means comprises a piston slidingly received in the inflation chamber in sealing engagement with walls defining the inflation chamber, the means for operatively connecting the actuating means and the valve means comprising the valve means being provided in the piston and the walls defining the inflation chamber.

40. A cardioplegia administration system according to claim 28 further comprising a switch housing having the walls defining the inflation chamber, the piston having side walls generally adjacent the walls defining the inflation chamber and movable therealong, the valve means comprising:

a retrograde passageway through the wall defining the inflation chamber, the retrograde passageway being in fluid communication with the retrograde tubing to provide cardioplegia solution to the retrograde catheter;

an antegrade passageway through the wall defining the inflation chamber, the antegrade passageway being in fluid communication with the antegrade tubing to provide cardioplegia solution to the antegrade catheter;

a cardioplegia supply passageway through the wall defining the inflation chamber, the cardioplegia supply passageway being in fluid communication with the cardioplegia supply tubing to provide cardioplegia solution to the cardioplegia supply passageway; and a valve passageway defined by the piston, the valve passageway bringing the cardioplegia supply passageway and antegrade passageway into fluid communication when the piston is in its first position, and the valve passageway bringing the cardioplegia supply passageway and retrograde passageway into fluid communication when the piston is in its second position.

41. A cardioplegia administration system according to claim 40 wherein the piston prevents fluid communication between the retrograde passageway and cardioplegia supply passageway when the piston is in its first position, and the piston prevents fluid communication between the antegrade passageway and the cardioplegia supply passageway when the piston is in its second position.

42. A cardioplegia administration system according to claim 41 further comprising a lever pivotable mounted on the switch housing and operatively connected to the piston to move the piston between its first and second positions.

43. A cardioplegia administration system according to claim 42 further comprising a rod extending from the piston and having a rack portion with teeth, and a pinion on the lever, the pinion having teeth in intermeshing engagement with the teeth of the rack portion of the rod to move the piston as the lever is pivoted.

44. A cardioplegia administration system according to claim 43 wherein the piston has a circumference and at least two annular sealing rings extending along the circumference of the piston and defining the valve passageway along the circumference of the piston between the two annular sealing rings.

45. A cardioplegia administration system according to claim 38 further comprising means for releasably retaining the actuating means in either of its first and second positions.

46. A cardioplegia administration system according to claim 38 wherein the balloon inflation means of the switch comprises a syringe defining the inflation chamber and having a plunger, constituting the actuating means, movable within the inflation chamber for pressurizing and depressurizing the retention balloon of the retrograde catheter.

47. A cardioplegia administration system according to claim 38 wherein the valve means of the switch comprises:
    a valve chamber having an inlet, a retrograde outlet adapted to be in fluid communication with infusion lumen of the retrograde catheter, and an antegrade outlet adapted to be in fluid communication with the infusion lumen of the antegrade catheter; and
    a valve member movable within the valve chamber between a first position, wherein the antegrade outlet is in fluid communication with the inlet of the valve chamber and the retrograde outlet is blocked, and a second position, wherein the retrograde outlet is in fluid communication with the inlet of the valve chamber and the antegrade outlet is blocked;
    the actuating means and the valve member being operatively connected such that the valve member is in its first position when the actuating means is in its first position and the valve member is in its second position when the actuating means is in its second position.

48. A cardioplegia administration system according to claim 47 wherein the actuating means of the switch comprises a first plunger movable within the inflation chamber along a first longitudinal axis of motion between its first and second positions, and the valve member comprises a second plunger movable within the valve chamber along a second longitudinal axis of motion generally parallel with the first longitudinal axis of motion between its first and second positions in generally the same direction as the first plunger;
    the first and second plungers being connected together such that the first and second plungers are simultaneously moved in generally the same direction between the first and second positions.

49. A cardioplegia administration system according to claim 48 wherein the means for operatively connecting the actuating means and the valve means comprises a single handle, operatively linking the first and second plungers, for manually and simultaneously moving the first and second plungers between their first and second positions.

50. A cardioplegia administration system according to claim 49 wherein:
    the balloon inflation means of the switch further comprises a first housing defining the inflation chamber as being generally elongate having a longitudinal axis coaxial with the first longitudinal axis of motion of the first plunger;
    the valve means further comprises a valve housing defining the valve chamber as being generally elongate having a longitudinal axis coaxial with the second longitudinal axis of motion of the second plunger and generally parallel with the longitudinal axis of the inflation chamber, the valve chamber having opposite ends; and
    the retrograde and antegrade outlets being located generally adjacent the opposite ends of the valve chamber relative to one another, and the inlet being located generally between the retrograde and antegrade outlets, the second plunger when in its first position being positioned between the inlet and the retrograde outlet to block passage of cardioplegia solution through the retrograde outlet, and the second plunger when in its second position being positioned between the inlet and the antegrade outlet to block passage of cardioplegia solution through the antegrade outlet.

51. A cardioplegia administration system according to claim 50 wherein the inflation chamber has opposite ends generally adjacent the opposite ends of the valve chamber, the opposite ends of each of the inflation and valve chambers of the switch comprising:
    a first end, with the handle extending outwardly from the first ends of the inflation and valve chambers, the retrograde outlet of the valve chamber being generally adjacent the first end of the valve chamber; and
    a second end, with the port of the inflation chamber extending from the second end, the antegrade outlet of the valve chamber being generally adjacent the second end of the valve chamber.

52. A cardioplegia administration system according to claim 51 wherein the inflation chamber of the switch is defined by a generally cylindrical internal wall of the first housing, and the valve chamber is defined by a generally cylindrical internal wall of the valve housing.

53. A cardioplegia administration system according to claim 52 wherein the first and second plungers comprise elastomeric sealing members in sealing engagement with the internal walls defining the inflation chamber and the valve chamber, respectively.

54. A cardioplegia administration system according to claim 52 wherein the first housing and valve housing are integrally molded in one piece.

55. A cardioplegia administration system according to claim 54 wherein the port, inlet, antegrade outlet and retrograde outlet of the switch each further comprises connection means for connecting with balloon-inflation tubing, the cardioplegia supply tubing, the antegrade tubing and the retrograde tubing.

56. A cardioplegia administration system for selectively administering cardioplegia solution to a patient's heart in the antegrade direction via the arterial system of the heart or in the retrograde direction via the venous system of the heart, the system comprising:
    an antegrade catheter having an infusion lumen for administering cardioplegia solution to a patient's heart via the arterial system of the heart in the antegrade direction;

antegrade tubing in fluid communication with the infusion lumen of the antegrade catheter for providing cardioplegia solution to the infusion lumen of the antegrade catheter;

a retrograde catheter having an infusion lumen for administering cardioplegia solution to a patient's heart via the venous system of the heart in the retrograde direction, an inflatable retention balloon for retaining the retrograde catheter in position in the patient's heart, and a inflation lumen in fluid communication with the balloon for providing fluid to the balloon to inflate the balloon and for draining fluid from the balloon to deflate the balloon;

retrograde tubing in fluid communication with the infusion lumen of the retrograde catheter for providing cardioplegia solution to the infusion lumen of the retrograde catheter;

balloon-inflation tubing in fluid communication with the inflation lumen of the retrograde catheter for supplying and draining fluid to and from the retention balloon to inflate and deflate the retention balloon;

a source of cardioplegia solution;

cardioplegia supply tubing in fluid communication with the source of cardioplegia solution; and an antegrade/retrograde switch for selectively directing cardioplegia solution to either one of the antegrade and retrograde catheters, the switch comprising:

a housing having internal walls defining an inflation chamber and a valve chamber, the housing having:

a port into the inflation chamber and a first connector on the port for connecting the balloon-inflation tubing in fluid communication with the inflation chamber;

an inlet into the valve chamber and a second connector on the inlet for connecting the cardioplegia supply tubing in fluid communication with the valve chamber;

a retrograde outlet from the valve chamber and a third connector on the retrograde outlet for connecting retrograde tubing in fluid communication with the valve chamber; and an antegrade outlet from the valve chamber and a fourth connector on the antegrade outlet for connecting the antegrade tubing in fluid communication with the valve chamber; and an actuator member in the inflation chamber in sealing engagement with the walls of the housing defining the inflation chamber; and a valve member in the valve chamber in sealing engagement with the walls of the housing defining the valve chamber;

the actuator member and valve member being operatively linked for movement between:

a first position, wherein the actuator member is spaced from the port of the inflation chamber and the retention balloon of the retrograde catheter is deflated, and the valve member is positioned between the inlet and the retrograde outlet to direct cardioplegia solution from the inlet through the antegrade outlet; and a second position, wherein the actuating member is closer to the port of the inflation chamber than in the first position to inflate the retention balloon of the retrograde catheter, and the valve member is positioned between the inlet and the antegrade outlet to direct cardioplegia solution from the inlet through the retrograde outlet.

57. A cardioplegia administration system according to claim 56 wherein the switch further comprises a single handle, operatively linked with the actuating member and valve member, for manually moving the actuating member and valve member between the first and second positions.

58. A cardioplegia administration system according to claim 57 wherein the internal walls of the switch defining the inflation chamber and valve chamber are each generally cylindrical, the actuating member and valve member each including generally circular elastomeric sealing means in sealing engagement with the internal walls defining the inflation chamber and valve chamber, respectively.

59. A cardioplegia administration system according to claim 58 wherein actuating member and valve member of the switch each further include a rod linking the actuating member and valve member, respectively, with the single handle.

60. A cardioplegia administration system according to claim 59 wherein the housing of the switch is integrally molded of synthetic resin material.

61. A cardioplegia administration system according to claim 59 wherein:

the inflation chamber is generally elongate having a longitudinal axis, the actuating member moving between the first and second positions along a first longitudinal axis of motion coaxial with the longitudinal axis of the inflation chamber;

the valve chamber is generally elongate having a longitudinal axis, the valve member moving between the first and second positions along a second longitudinal axis of motion coaxial with the longitudinal axis of the valve chamber and generally parallel with the longitudinal axis of the inflation chamber, the valve chamber having opposite ends; and the retrograde and antegrade outlets are located generally adjacent the opposite ends of the valve chamber relative to one another, the inlet being located generally between the retrograde and antegrade outlets, the valve member when in the first position being positioned between the inlet and the retrograde outlet to block passage of cardioplegia solution through the retrograde outlet, and the valve member when in the second position being positioned between the inlet and the antegrade outlet to block passage of cardioplegia solution through the antegrade outlet.

62. A cardioplegia administration system according to claim 61 wherein the inflation chamber has opposite ends generally adjacent the opposite ends of the valve chamber, the opposite ends of each of the inflation chamber and valve chamber comprising:

a first end, with the rods extending outwardly from the first ends of the inflation and valve chambers to the single handle, the retrograde outlet of the valve chamber being generally adjacent the first end of the valve chamber; and a second end, with the port of the inflation chamber extending from the second end of the inflation chamber, the antegrade outlet of the valve chamber being generally adjacent the second end of the valve chamber.

* * * * *

UNITED STATES PATENT AND TRADEMARK OFFICE
CERTIFICATE OF CORRECTION

PATENT NO.: 5,755,686

DATED: May 26, 1998

INVENTOR(S): William G. O'Neill, Nelson L. Huldin and Lawrence R. Jones

It is certified that error appears in the above-identified patent and that said Letters Patent is hereby corrected as shown below:

Col. 19, line 7, "claim 12" should read --claim 14--.

Col. 24, line 42, "claim 28" should read --claim 39--.

Signed and Sealed this

Twenty-second Day of September, 1998

Attest:

BRUCE LEHMAN

*Attesting Officer*   *Commissioner of Patents and Trademarks*